(12) United States Patent
Hatcher et al.

(10) Patent No.: US 8,337,893 B2
(45) Date of Patent: Dec. 25, 2012

(54) SOL-GEL DERIVED BIOACTIVE GLASS POLYMER COMPOSITE

(75) Inventors: Brian M. Hatcher, Gainesville, FL (US); Anthony Brennan, Gainesville, FL (US); Brian Cuevas, Middletown, CT (US); Charles Seegert, San Antonio, TX (US)

(73) Assignee: Florida Research Foundation, Inc, University Of, Gainesville, FL (US)

( * ) Notice: Subject to any disclaimer, the term of this patent is extended or adjusted under 35 U.S.C. 154(b) by 2114 days.

(21) Appl. No.: 10/616,884

(22) Filed: Jul. 10, 2003

(65) Prior Publication Data

US 2004/0052861 A1 Mar. 18, 2004

Related U.S. Application Data

(60) Provisional application No. 60/395,186, filed on Jul. 10, 2002.

(51) Int. Cl.
  *A61K 9/14* (2006.01)
  *A61K 47/02* (2006.01)
(52) U.S. Cl. .................. 424/485; 424/484; 424/486
(58) Field of Classification Search .................. 424/422, 424/57, 423, 426, 602, 457, 484–486; 514/421, 514/12
  See application file for complete search history.

(56) References Cited

U.S. PATENT DOCUMENTS

| | | | |
|---|---|---|---|
| 5,316,695 A | | 5/1994 | Wilkes |
| 5,338,772 A | * | 8/1994 | Bauer et al. .................. 523/115 |
| 5,532,217 A | | 7/1996 | Silver et al. .................. 514/21 |
| 5,591,453 A | * | 1/1997 | Ducheyne et al. ............ 424/484 |
| 5,645,934 A | | 7/1997 | Marcolongo et al. |
| 5,676,720 A | * | 10/1997 | Ducheyne et al. ............ 65/17.5 |
| 5,711,960 A | * | 1/1998 | Shikinami .................. 424/426 |
| 5,721,049 A | * | 2/1998 | Marcolongo et al. ......... 428/370 |
| 5,747,390 A | * | 5/1998 | Cooper et al. .................. 442/59 |
| 5,916,686 A | | 6/1999 | Lin |
| 5,977,204 A | | 11/1999 | Boyan et al. |
| 5,990,380 A | * | 11/1999 | Marotta et al. ............. 623/11.11 |
| 6,027,742 A | * | 2/2000 | Lee et al. .................. 424/422 |
| 6,121,172 A | | 9/2000 | Marcolongo et al. |
| 6,147,135 A | * | 11/2000 | Yuan et al. .................. 523/105 |
| 6,180,248 B1 | | 1/2001 | Basil |
| 6,210,715 B1 | | 4/2001 | Starling et al. |
| 6,294,041 B1 | * | 9/2001 | Boyce et al. ................ 156/275.5 |
| 6,328,990 B1 | * | 12/2001 | Ducheyne et al. ............ 424/426 |
| 6,344,496 B1 | * | 2/2002 | Niederauer et al. .......... 523/113 |
| 6,386,002 B1 | | 5/2002 | Bhandarkar |
| 6,413,538 B1 | | 7/2002 | Garcia et al. |
| 2001/0016353 A1 | * | 8/2001 | Janas et al. .................. 435/395 |

OTHER PUBLICATIONS

Oréfice, et al., "Novel sol-gel bioactive fibers," Journal of Biomedical Materials Research, 55(4):460-467, 2001.
Domingues et al., "A sol-gel derived bioactive fibrous mesh," Journal of Biomedical Materials Research, 55(4):468-474, 2001.
Brinker et al., "Sol-Gel Science: The Physics and Chemistry of Sol-Gel Processing," San Diego: Academic Press, 1990.
Otsubo, Y., "Rheology of colloidal suspensions flocculated by reversible bridging," Chemical Engineering Science, 56:2939-2946, 2001.
Ågren et al., "Phase Behavior and Structural Changes in Tetraethylorthosilicate-Derived Gels in the Presence of Polyethylene Glycol, Studied by Rheological Techniques and Visual Observations," Journal of Colloid and Interface Science, 204:45-52, 1998.
Biggs et al., "Aggregate structures formed via a bridging flocculation mechanism," Chemical Engineering Journal, 80:13-22, 2000.
Kokubo et al., "Solutions able to reproduce in vivo surface-structure changes in bioactive glass-ceramic A-W3," Journal of Biomedical Materials Research, 24:721-734, 1990.
Yuan et al., "Bone Induction by Porous Glass Ceramic Made from Bioglass (45S5)," Journal of Biomedical Materials Research, 58:270-276, 2001.
Smith et al., "Calcium Phosphate Hydroxide," JCPDS International Center for Diffraction Data, CAS#1306-06-5-1996.
Sircarl, A., "An introduction to glass and glass fiber manufacturing technology with application to nonwoven process," Tappi Journal 76:167-175, 1993.

* cited by examiner

*Primary Examiner* — Michael G Hartley
*Assistant Examiner* — Micah-Paul Young
(74) *Attorney, Agent, or Firm* — Cantor Colburn LLP

(57) ABSTRACT

A bioactive sol-gel solution includes a biocompatible polymer, a gelable inorganic base material, and at least one calcium and phosphorous molecular species. The base material can be an alkoxide, such as TEOS. The polymer acts as a viscosity modifier to the sol or gel, increases the viscosity range over which fibers can be sprayed or spun, and broadens the time period over which fibers can be sprayed or spun. A bioactive glass composite can be formed from the bioactive sol-gel solution, including a fibrous form. Fibers can serve as a scaffold for cell growth and in the repair of hard or soft tissue defects.

33 Claims, 27 Drawing Sheets

SB = 1cm

250x SEM

25μm Array. SB = 250μm

55μm Array. SB = 250μm

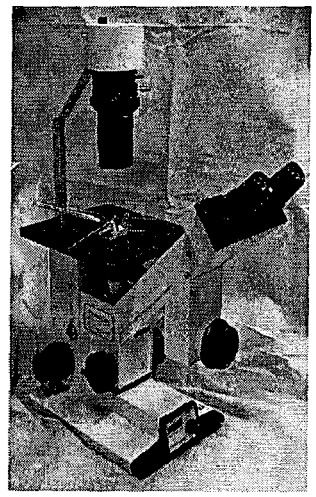 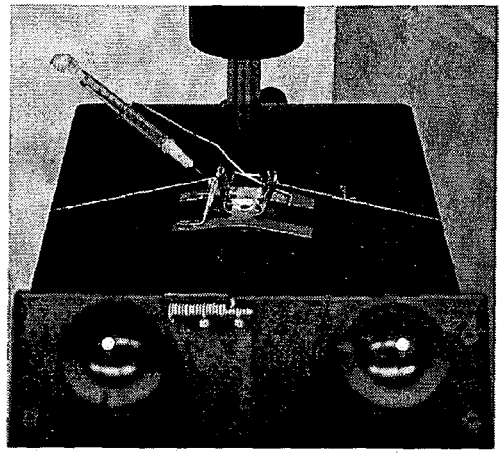
FIG. 27A            FIG. 27B
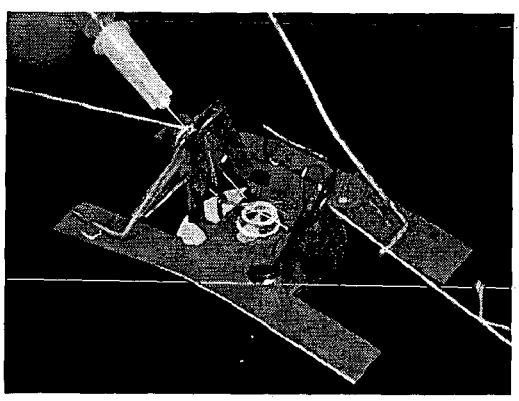 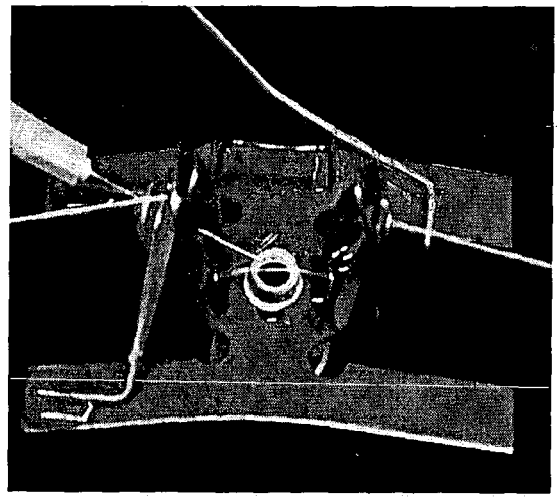
FIG. 27C            FIG 27D

SOL-GEL DERIVED BIOACTIVE GLASS POLYMER COMPOSITE

CROSS-REFERENCE TO RELATED APPLICATIONS

This application claims the benefit of U.S. Provisional Application 60/395,186 entitled "Sol-gel Bioactive Glass and its Production Using Polymer Enhanced Control of Rheological Behavior and Sol Stabilization" filed Jul. 10, 2002, the entirety of which is incorporated herein by reference.

STATEMENT REGARDING FEDERALLY SPONSORED RESEARCH OR DEVELOPMENT

Not applicable

FIELD OF THE INVENTION

The invention relates to sol-gel based polymer comprising composite materials, and methods for forming and using the same.

BACKGROUND OF THE INVENTION

The incorporation of materials science, cellular biology and engineering together with other fields such as chemistry and biochemistry has contributed to the expansion of modern medicine. The integration of the physical and life sciences helps address a number of the key issues in fields such as biomaterials and tissue engineering with the goal of bringing functional and practical devices or implants to the patient. Engineered tissue scaffolds and implantable materials must maintain physical and mechanical properties necessary to withstand the dynamic conditions present within the body and be biocompatible.

A number of materials and a variety of scaffold designs have been investigated for use as tissue engineering matrices for bone regeneration applications. Ideally, the scaffold is a porous, three-dimensional structure capable of maintaining structural integrity and allowing for cellular influx, growth, extracellular matrix (ECM) deposition, and metabolic exchange. The properties of the scaffold should be tailorable to control degradation rate, degree of porosity, and mechanical strength in order to closely match that of the host tissue. The scaffold material should not stimulate an adverse immunological response through chemical species present at the implant surface or through possible degradation byproducts (i.e. act as a biocompatible or bioactive material). To date, a number of synthetic polymers have been examined for their ability to serve as tissue engineering scaffolds. These materials have been examined in a number of forms such as particles, foamed porous scaffolds, and fibers, for their ability to initiate bone formation both in vitro an in vivo.

The use of bioactive glass fibers as tissue engineering scaffolds for the regeneration of new bone offers a number of advantages over the other forms mentioned above. The chemistry of this system is such that an immunological response is avoided and instead replaced with a bioactive mechanism. The bioactive glass fibers can undergo a series of chemical reactions leading to the precipitation of a hydroxyapatite (HA) layer on their surface, resulting in a chemical bond to the host tissue (Hench, L L and Wilson, J., "An Introduction to Bioceramics", World Scientific, 1993). The bioactive glass in turn becomes an integral part of the native tissue. Fabrication of a bioactive glass scaffolds constructed of fibers can provide the necessary structural integrity to maintain mechanical stability while at the same time allowing for the control of porosity, surface area, degradation rate, and the contact guidance of cells. The fibrous system mimics that of the natural collagen fibers orthogonally distributed within native bone providing it with enhanced strength. It is on these collagen fibrils that HA is deposited. In addition, the synthetic nature of the system allows for ease in production, transport and sterilization make it an attractive option as a tissue engineering scaffold.

Bioactive glass fibers have a relatively high silica content that limits their production by the classical high temperature commercial process due to extremely high melt viscosities (Silcar, A., "An Introduction to Glass and Glass Fiber Manufacturing Technology with Application to Nonwoven Process", Tappi J., 1993; 76:167-174). $Na_2O$ and $CaO$ are usually necessary coreactants in conventional processing to adjust the viscosity to levels compatible with fiber pulling. However, the high concentration of $Na_2O$ and $CaO$ in bioactive glasses induces crystallization, which ultimately limits the biological activity. Therefore, tradeoffs are generally required.

One way to overcome this problem is through the use of a sol-gel process, as opposed to a melt process, to produce fibers. The sol-gel process uses lower processing temperatures which can reduce crystallization. A sol-gel process involves reactions of hydrolysis and condensation on metal alkoxides that lead to the formation of inorganic chains, rings, and clusters. These reactions can be controlled to produce the required sol structure (colloidal suspension) necessary to fabricate materials such as fibers, films, powders, and gels. Initial conditions of hydrolysis and condensation, such as pH and concentration of agents, can be used to adjust the resulting sol structure.

With regard to fiber pulling, the rheological behavior of the sol is one of the most important processing variables. It is basically accepted that elongated polymers in a solution is the main requirement for spinnability.

Acidic pH values and low molar ratios between water and alkoxide are known to produce linear polymers that exhibit spinnability. On the other hand, high molar ratios between water/alkoxide and a basic medium led to production of spherical and ramified polymers that yield network formation. A low molar ratio of water/alkoxide (2:1) favors generation of a functionality of 2 in the inorganic polymers. The functionality of 2, in this case, refers to the conversion of alkoxide groups to hydroxyl groups, which are more readily condensed and will produce a "linear" polymeric precursor of the sintered fiber. A higher functionality will lead to particle formation, which is undesirable for fiber production. An acidic medium reduces the immiscibility gap in the alcohol-alkoxide-water system and provides a catalytic effect that is also important in the development of linear polymers.

Another important parameter of sol-gel fiber processing that should be optimized is the time between the onset of the spinnability and the gelation time. Disclosed formulations generally exhibit very short gelation times which restrict the production of continuous fibers and the process efficiency.

SUMMARY OF THE INVENTION

The invention concerns a bioactive sol solution, a bioactive gel, and bioactive glass (BG), each combined with a biocompatible polymer to form a composite, and methods for producing the same. The BG composite can be provided in a variety of forms, including fibers, particulates, spheres, coatings, and foamed scaffolds.

The term "biocompatible", as used herein, means that the material does not elicit a substantial detrimental response in the host. It should be appreciated that when a foreign object is introduced into a living body, that the object may induce an immune reaction, such as an inflammatory response that may have negative effects on the host. As used herein, the term "biocompatible" is intended to include those materials that may cause some inflammation, but do not rise to the level of pathogenesis. Preferably, the composites of the subject invention are also biocompatible.

A polymer is incorporated in the synthesis of the bioactive glass (BG) sol. Advantageously, the polymer acts as a viscosity modifier to the sol or gel, increases the viscosity range over which fibers can be sprayed or spun, and broadens the time period over which fibers can be sprayed or spun.

The polymer may be a polymer that possesses a charge. However, interactions such as van der Waals and Hydrogen bonding also may play an important role in the interactions and stability generated by compositing the polymer with the bioactive glass sol.

A bioactive sol-gel solution comprises a biocompatible polymer, a gelable inorganic base material, and at least one calcium and phosphorous molecular species. The base material can be an alkoxysilane alkoxide, such as TEOS. Alternatively, the base material can be a non-alkoxysilane alkoxide, such as aluminates, titanates and borates. The polymer can be polyvinylpyrrolidone (PVP), polyethyleneimine (PEI), polycarboxylmethylcellulose (PCMC), polyethylenglycol (PEG), polypropylene oxide (PPO), polyvinylalcohol (PVA), polyacrylic acid (PAA), polymethylacrylic acid (PMAA) polystyrene sulfonic acid (PSSA) or gelatin.

The pH of the solution can be from 1 to 7, or in one embodiment from 1.2 to 2, such when the desired processing involves fiber spraying or spinning. The viscosity of the solution at 25 C is from 1.5 Pa sec. to 6.0 Pa sec. The solution can be stable for at least 30 days at 25 C, and more preferably for up to 120 days, or more.

The solution can include at least one biologically active agent, where the solution forms an encapsulation layer around the biological agent. The biological agent can be a drug or pharmaceutical agent.

A bioactive glass composite comprises a biocompatible polymer, a bioactive glass including at least one calcium and at least one phosphorous molecular species. The composite can be in the form of microfibers. The fibers can have a diameter of less than 100 μm, less than 50 μm, or less than 20 μm. Alternatively, the composite can be in the form of particles, microspheres, or coatings. The porosity of the composition can be at least 50%, such as 60%, 70%, 80%, 90% or 95%.

When seeded, a variety of cell types, such as mesenchymal stem cells (MSCs), can proliferate on the fibers. Although growth hormones can be used with the invention, cells can proliferate in the absence of any growth hormones. The fibrous constructs can be used for preferentially directing cell growth and extracellular matrix (ECM) deposition via contact guidance.

Respective fibers can be substantially equally spaced to form an organized scaffold. Proper spacing will allow for the influx of cells and vasculature, and provide spacings which will allow for cellular bridging and the generation of cell based tensions. The equality of spacing will depend on the method or organization and will vary for meshes, mats, or weaves. Woven constructs will provide the highest degree of order, with the lowest deviation between the average distance of spaced fibers. The spacing distance is generally micron scale, such as 100 μm, 50 μm, or 25 μm.

The composition can include at least one biologically active agent. In one embodiment, the composition forms an encapsulation layer around the biological agent. The encapsulated biologically active agent can be in the form of microcapsules, microspheres, microparticles, microfibers, sol gel matrices or reinforcing fibers. The encapsulation layer can be continuous and substantially non-porous, wherein a sustained release profile of the biologically active agent is provided. Alternatively, the biologically active agent can be adsorbed onto the surface of the composition or chemically attached to a surface of the composition.

The composition can include at least one protein. The protein can be collagen (including cross-linked collagen), fibronectin, laminin, elastin (including cross-linked elastin), osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor or skeletal growth factor.

In another embodiment of the invention, the composition is disposed on a surface of or integrated within a medical device adapted for implantation into a patient. The medical device can be a prosthetic device.

A method of repairing hard or soft tissue defects comprising the steps of applying a fiber composition comprising a biocompatible polymer, a bioactive glass including at least one calcium, and at least one phosphorous molecular species to a defect site on a patient. The composition can be in the form of microfibers, said fibers having a diameter of less than 100 μm, less than 50 μm, or less than 20 μm. The fibers can be substantially equally spaced to form an organized scaffold. The spacing can be less than 50 μm. The composition can be in the form of particles. Cells can proliferate on or around the composition in the absence of any growth hormones.

A method of forming a bioactive glass comprising the steps of mixing a biocompatible polymer, a gelable inorganic base material, and at least one calcium and phosphorous molecular species, and hydrolizing the mixture. The method can include the step of forming a plurality of fibers. The forming process can be performed at a temperature of no more than 200 C, such as at room temperature (25 C). The forming step can comprise air-spraying or an extrusion process.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 1 shows the temperature and pH variations of a 77S bioactive glass synthesized with polyvinylpyrrolidone (PVP).

FIG. 2 shows the viscosity profile for a sprayable 77S bioactive glass sol synthesized with PVP.

FIGS. 3A and 3B show images of sprayed 77S bioactive glass fibers synthesized with PVP. FIG. 3A shows an optical image (Scale Bar (SB)=2 cm) and FIG. 3B shows a 1300× SEM image. FIGS. 3C and 3D show images of spun 77S bioactive glass fibers synthesized with PVP. FIG. 3C shows an optical image (SB=1 cm) and FIG. 3D shows a 250×SEM image.

FIG. 4 shows a thermogram for non heat-treated 77S bioactive glass fibers synthesized with PVP.

FIGS. 5A-5F show scanning electron micrograph (SEM) images of sprayed 77S bioactive glass fibers submerged in simulated body fluid (SBF) for FIG. 5A: 0, FIG. 5B: 1, FIG.

5C: 5, FIG. 5D: 10, FIG. 5E: 20, and FIG. 5F 30 days. SB=10 microns in FIG. 5A and 20 microns in FIGS. 5B-5F.

Figure 8:
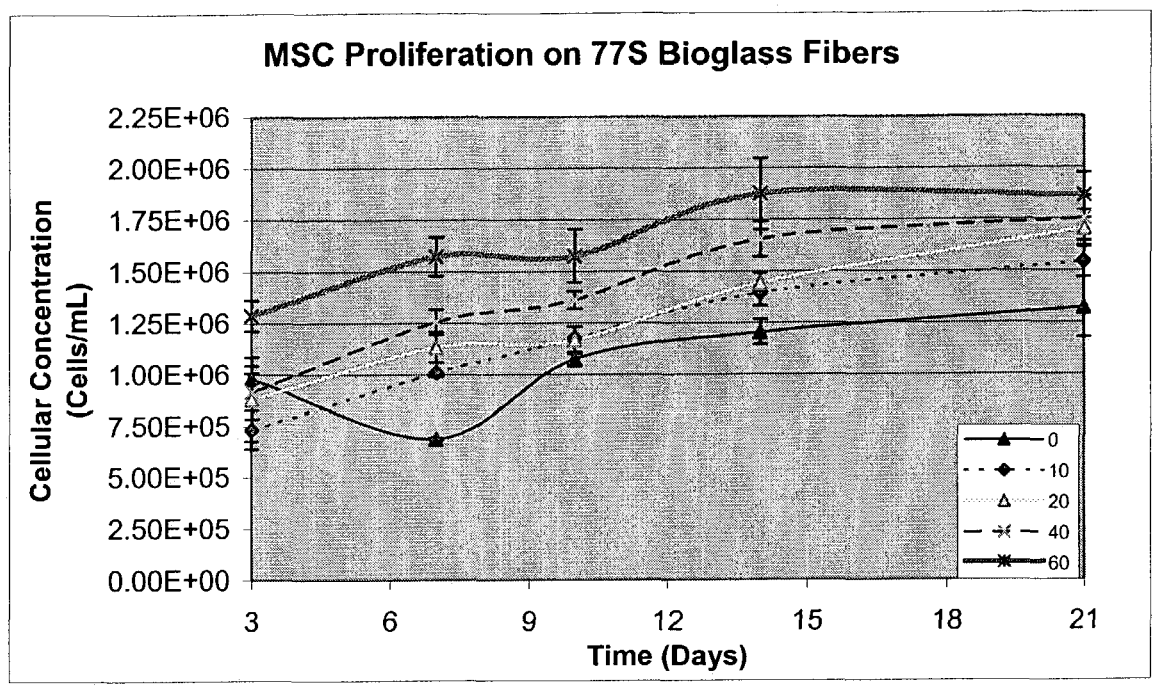

FIG. 8 shows rat MSC proliferation of 77S BG fiber constructs. Curves are plotted for the different fiber masses. The numbers 0, 10, 20, 40, and 60 refer to mg of fibers.

Figure 9:
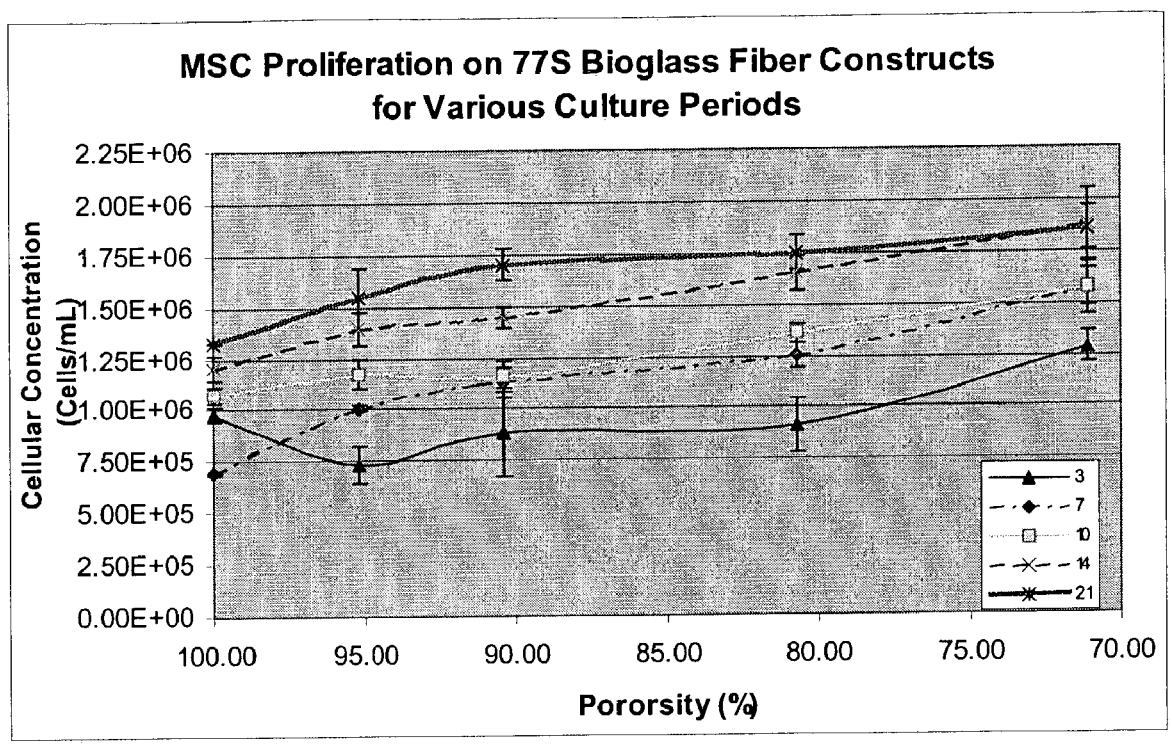

FIG. 9 shows rat MSC proliferation of 77S BG fiber constructs. Curves are plotted for the different time periods relative to construct porosity. The numbers 3, 7, 10, 14, and 21 refer to culture periods in days.

Figure 10:
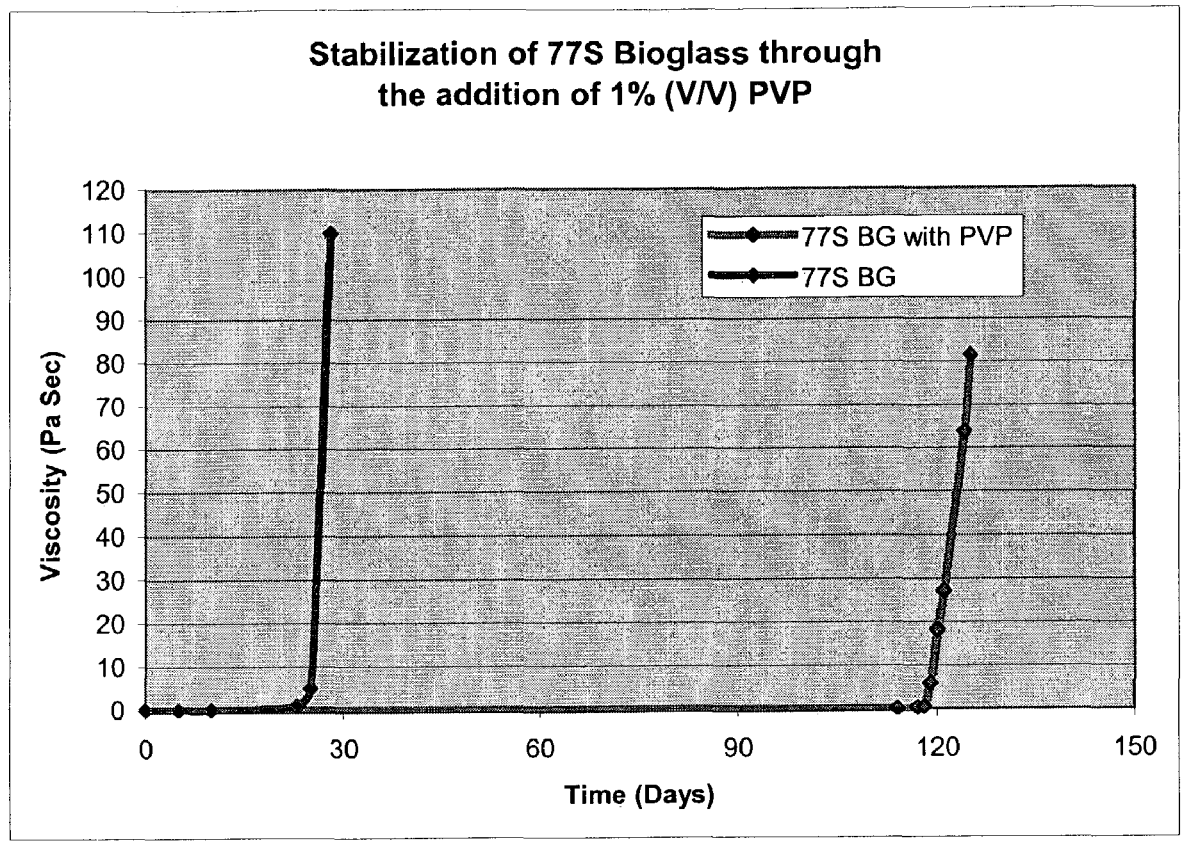

FIG. 10 shows the viscosity profile of both a stabilized 77S BG sol synthesized with PVP, and an unstabilized 77S sol.

Figure 11:
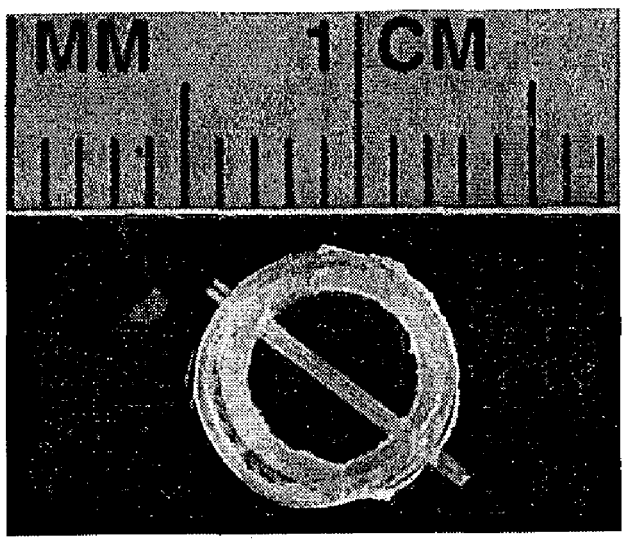
Figure 11:
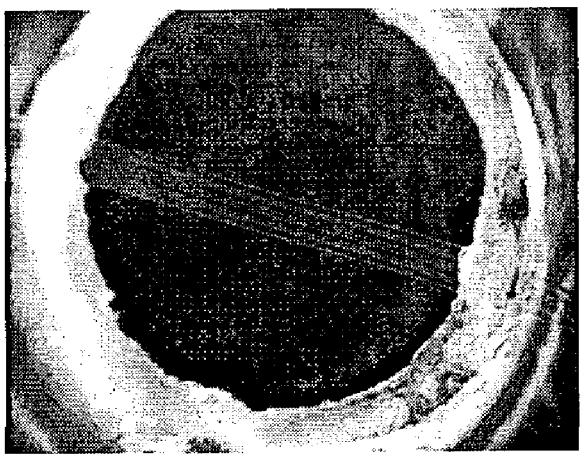
Figure 11:
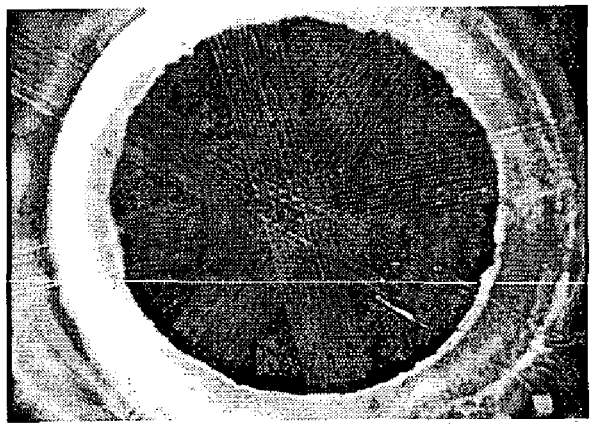

FIGS. 11A-11C show a multi-fiber construct composed of MAXON sutures. FIG. 11A shows a parallel array multi-fiber construct with 25 micron spacing and ruler for size reference. FIG. 11B shows a 25 micron parallel array with fibers visible. FIG. 11C shows a multi-layer, multi-fiber array with four lamellae.

Figure 12:
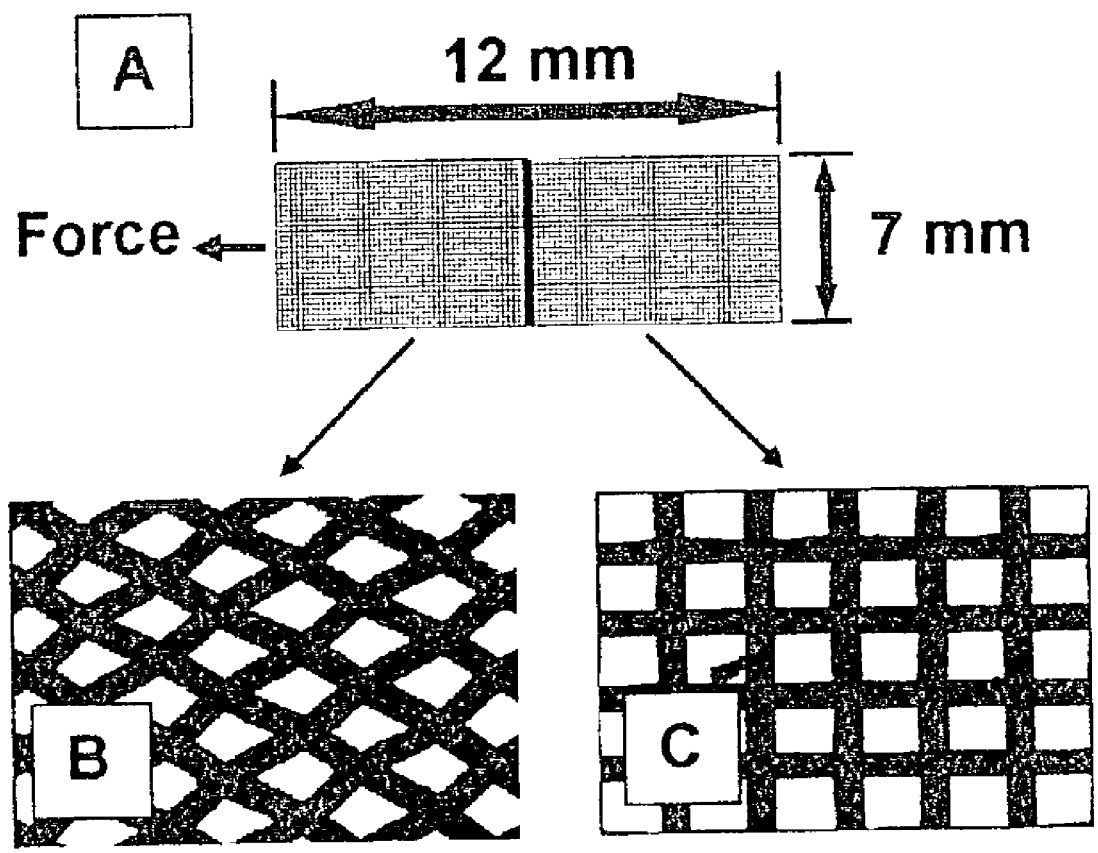

FIGS. 12A-12C show stainless steel construct schematics. FIG. 12A shows screens clamped in the center and pulled with pliers depicted by an arrow labeled Force. FIG. 12B shows elongated squares, or parallelograms produced by force application and imaged with light microscopy. FIG. 12C shows 90 degree control section of screen (magnification=40×).

Figure 13:
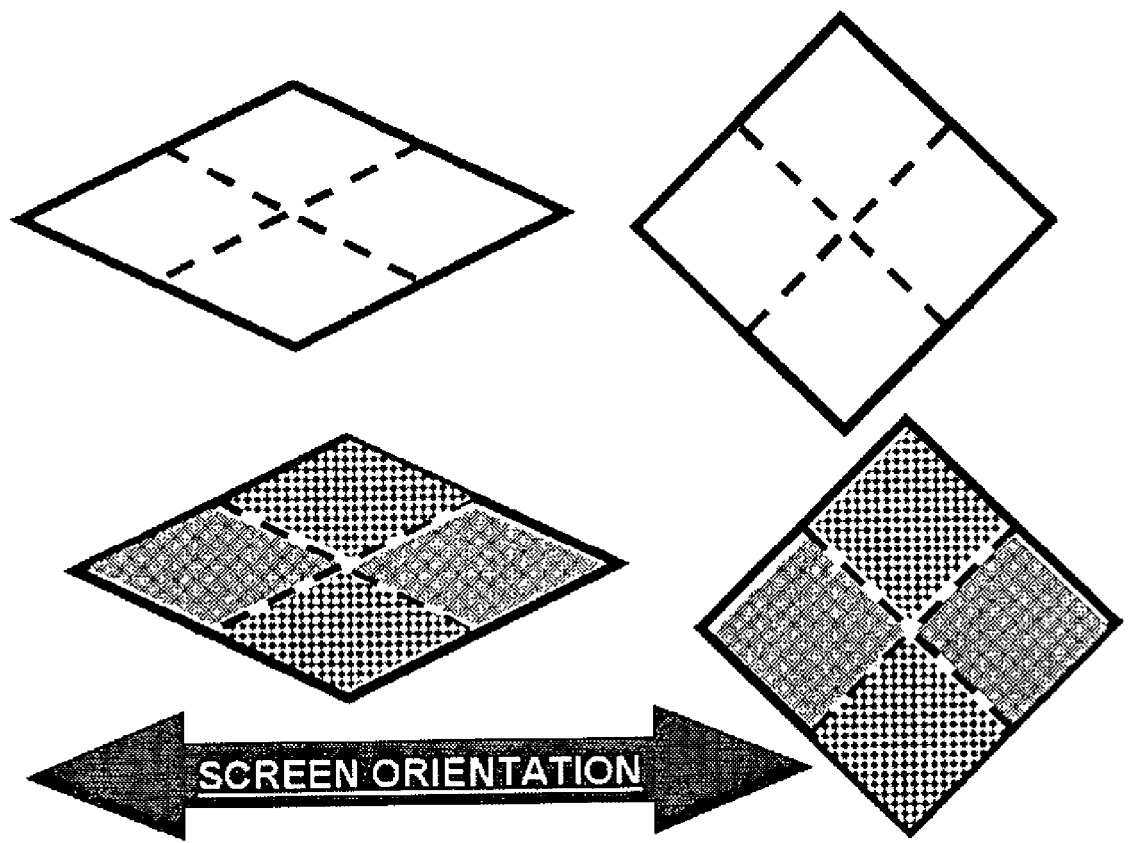

FIG. 13 shows schematic representation of parallelograms, in the case of the angled sections of the screen, and squares in the 90 degree portions. Data was collected from the same orientation within the total specimen. Finely hatched quadrants are equal to "Yes", or positive experiments in the binomial parameter test, coarser hatching areas equalling "No".

Figure 14A:
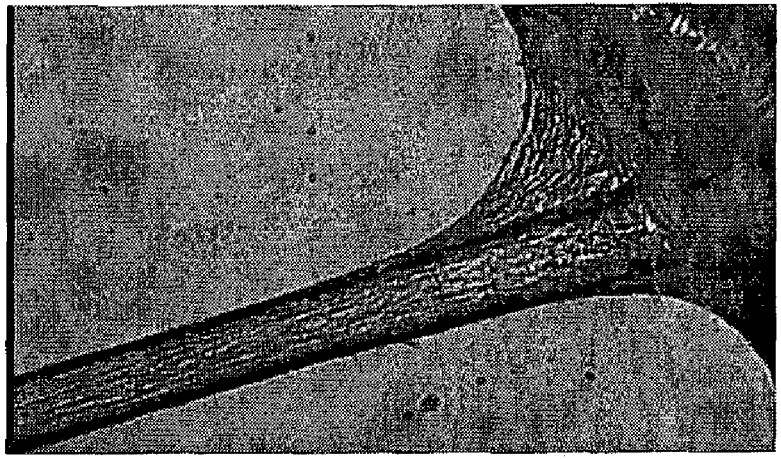
Figure 14B:
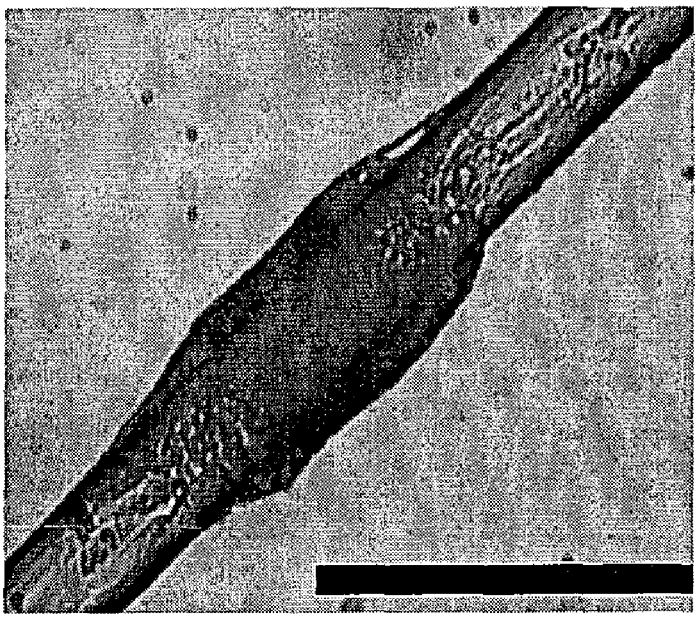

FIGS. 14A and 14B show a single fiber construct and a contracted area of cells on a single fiber. FIG. 14A shows a single fiber construct with heavy multi-layers of cells that are oriented in the direction of the fiber. Note the way cells bridge from the support ring to the fiber orienting in the direction of the ring and gradually, in a continuous manner changing their orientation in response to the fiber until they are aligned with it. FIG. 14B shows a contracted area of cells on a single fiber. Cells were originally like those seen in FIG. 14A. This contraction was not seen on the other single fiber in the same well.

Figure 15A:
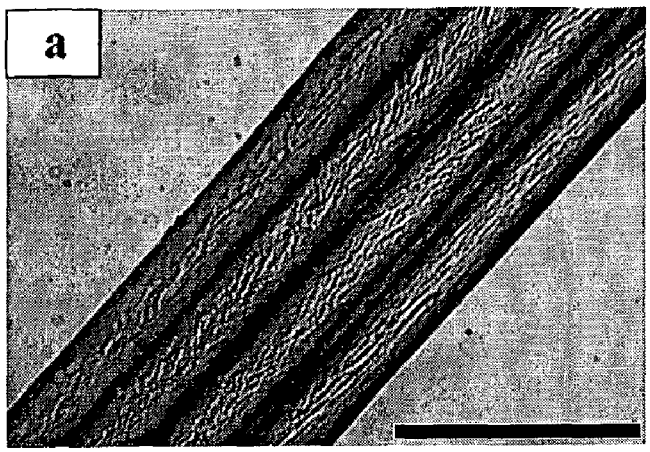
Figure 15B:
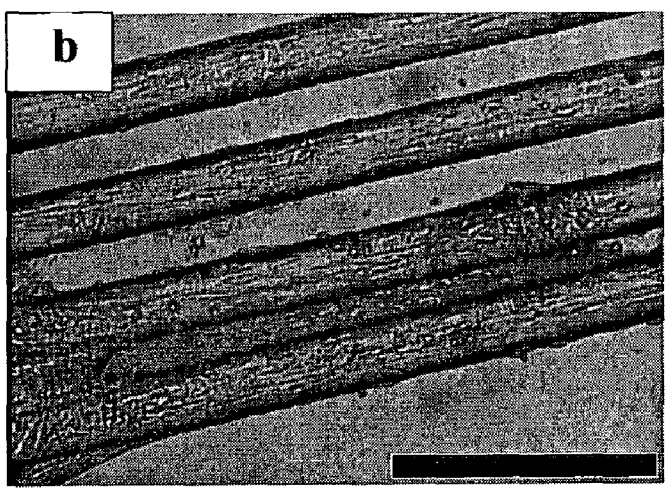

FIGS. 15A and 15B show multi-fiber bridging. FIG. 15A shows examples of spontaneous multi fiber bridging on a 25 micron parallel array. Note the way cells are oriented between fibers, their angle is very slight with respect to the fibers (arrowheads). FIG. 15B shows bridging on 55 micron parallel arrays near site of attachment to the support ring. This bridging developed using the support ring then separated. Note much sharper angles of the cells with respect to the fibers (arrowheads).

Figure 16A:
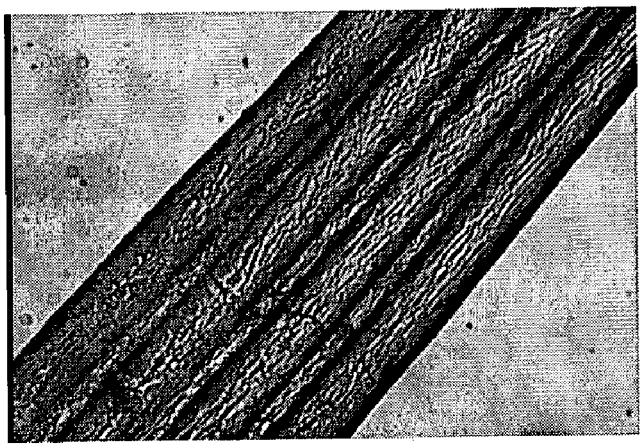
Figure 16B:
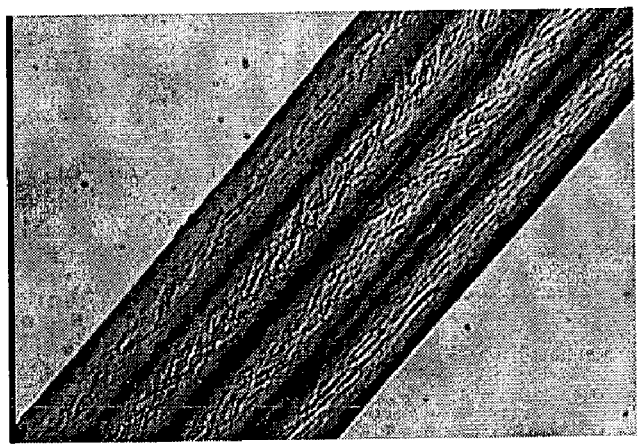
Figure 16C:
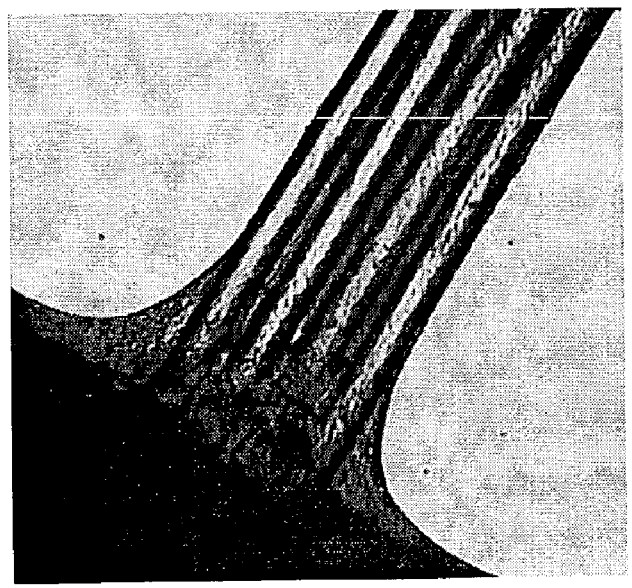

FIGS. 16A-16C show multi-fiber arrays. FIG. 16A shows a 25 micron parallel array with dense cell coverage. Cells are oriented in the direction of the fibers and spaces between fibers are completely filled. FIG. 16B shows a construct near the center of the fibers showing contraction and the drawing of fibers closer together. FIG. 16C shows an attachment site illustrating continuity of multi-cellular bridging similar to that seen on the single fiber constructs.

Figure 17A:
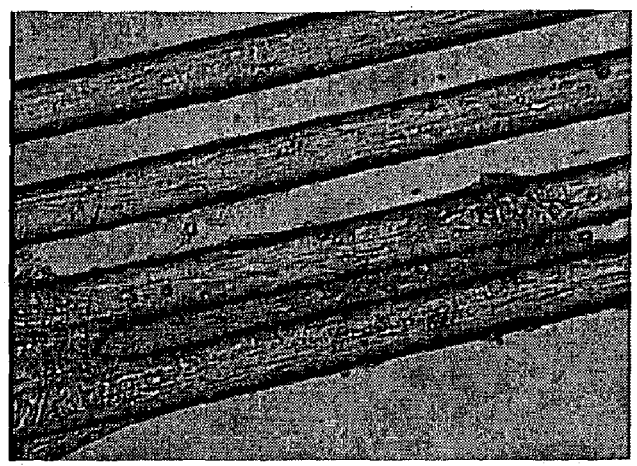
Figure 17B:
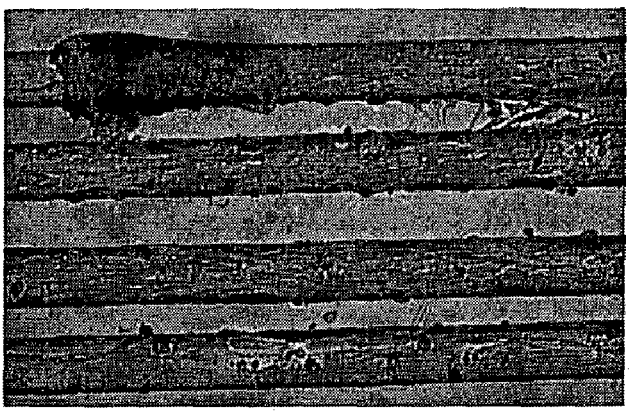
Figure 17C:
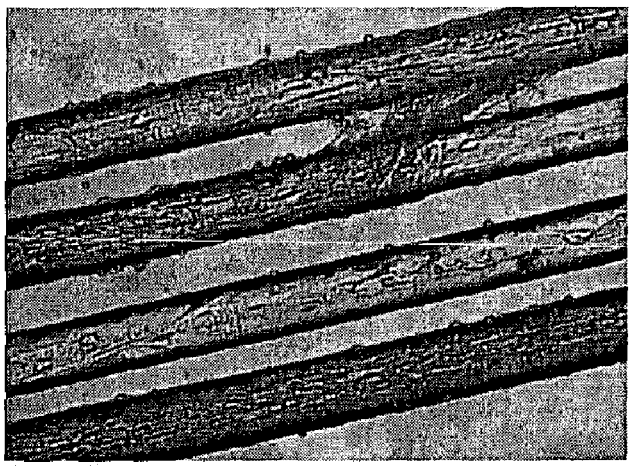

FIGS. 17A-17C show multi-cellular bridging. FIG. 17A shows an example of bridging originating from the support ring attachment on a 55 micron parallel array. FIG. 17B: top fiber shows a contractile process with the beginning of a bridge to the next lower fiber. Bridging to the right is from attachment site just outside the frame of the picture. FIG. 17C shows a multi-cellular bridge that formed after formation of a contractile process on the second fiber from the top. This image is taken 2 days after the contraction occurred and cells have begun to reorganize in the direction of the fibers.

Figure 18A:
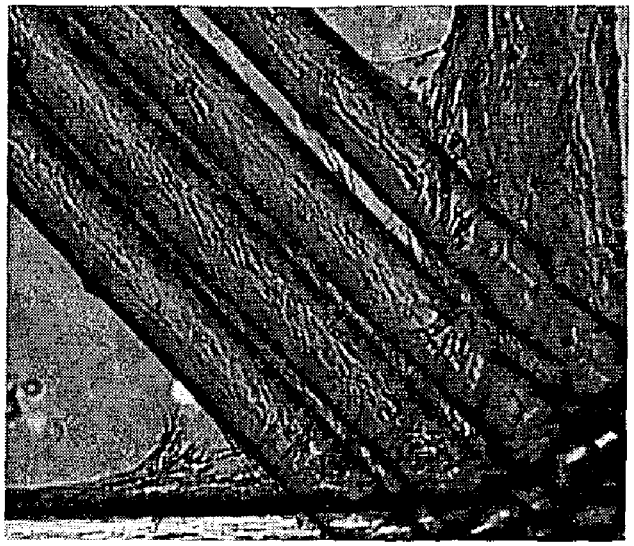
Figure 18B:
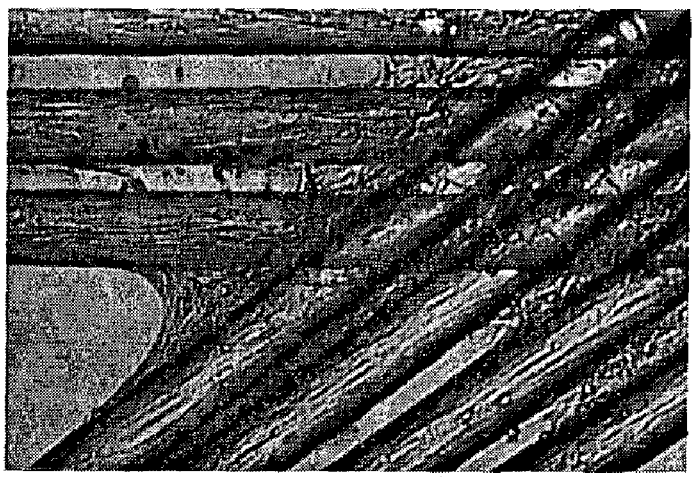

FIGS. 18A and 18B show multi-layer arrays. FIG. 18A shows a multi-layer array with 45 degree angles of rotation between layers. Bridging between fibers is apparent, as is bridging between layers. FIG. 18B shows that bridging seemed to preferentially form on acute angles versus obtuse. Bridging between these layers shows this preference in an area where bridging opportunities are possible in both the acute and obtuse angles, yet bridging occurs in the acute direction (arrowheads).

Figure 19:
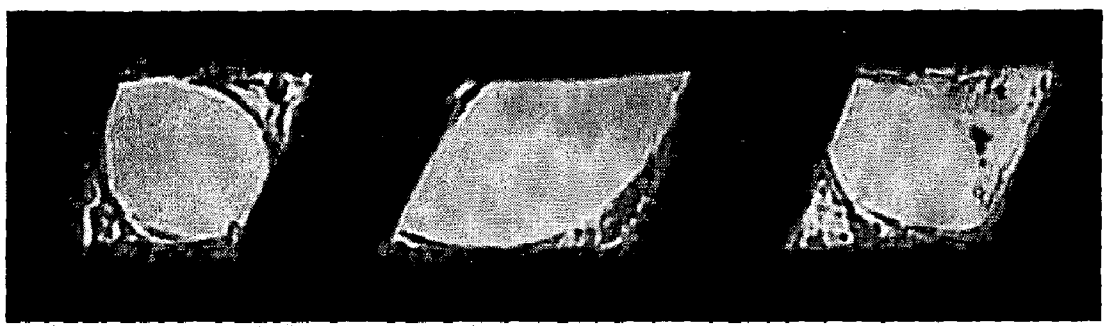

FIG. 19 shows an example of von Kossa stained, angled stainless steel screens with characteristic bridging on the acute angles. Mineralization is seen within the bodies of bridges formed in the angled junctions between fibers (see arrow pointers).

Figure 20:
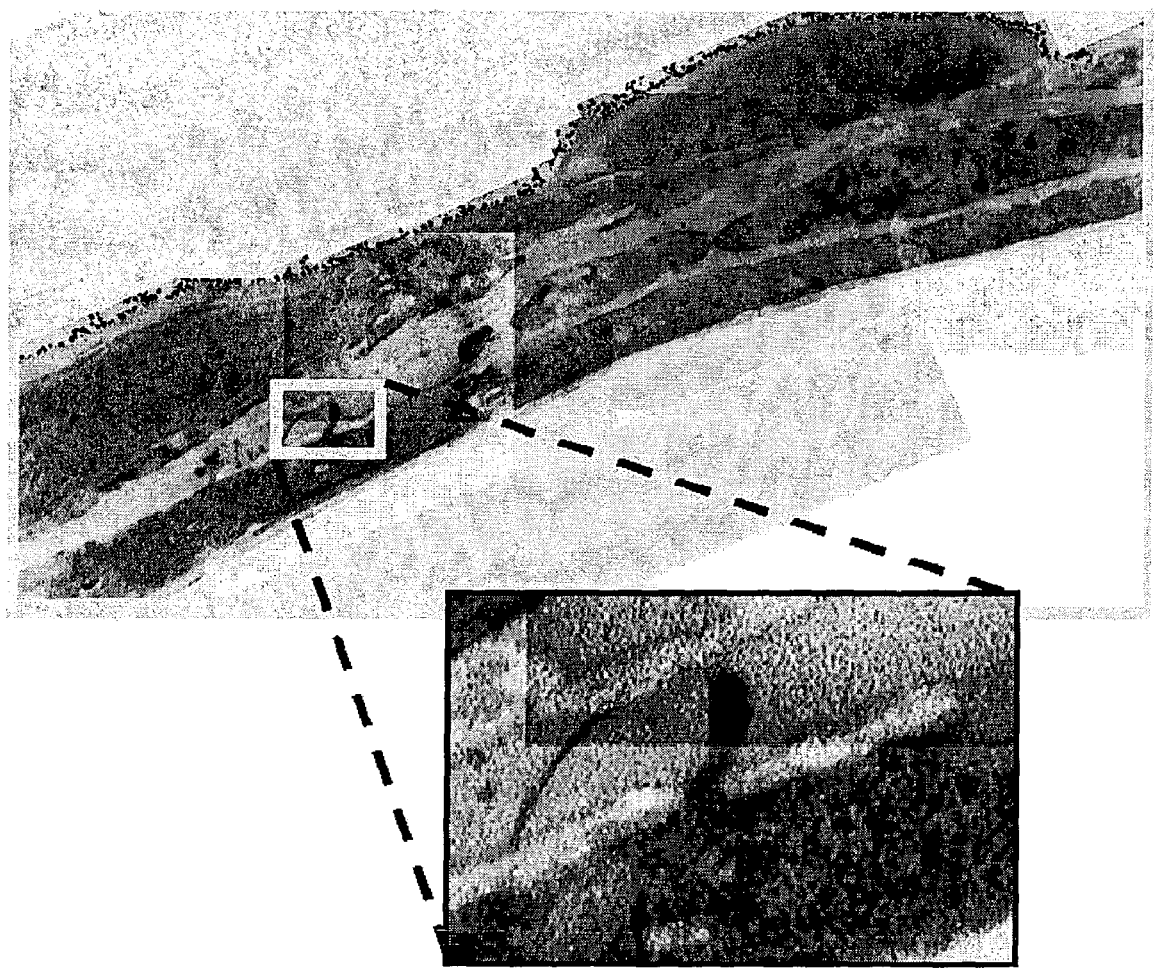

FIG. 20 shows a cell multi-layer on the surface of a single 7-0 fiber construct (magnification=3750×). Thickness of multi-layer is approximately 3-5 cells and the inset shows an inter-cellular communication, or what appears to be a pseudopod-like connection between cells (inset magnification=15,000×).

Figure 21:
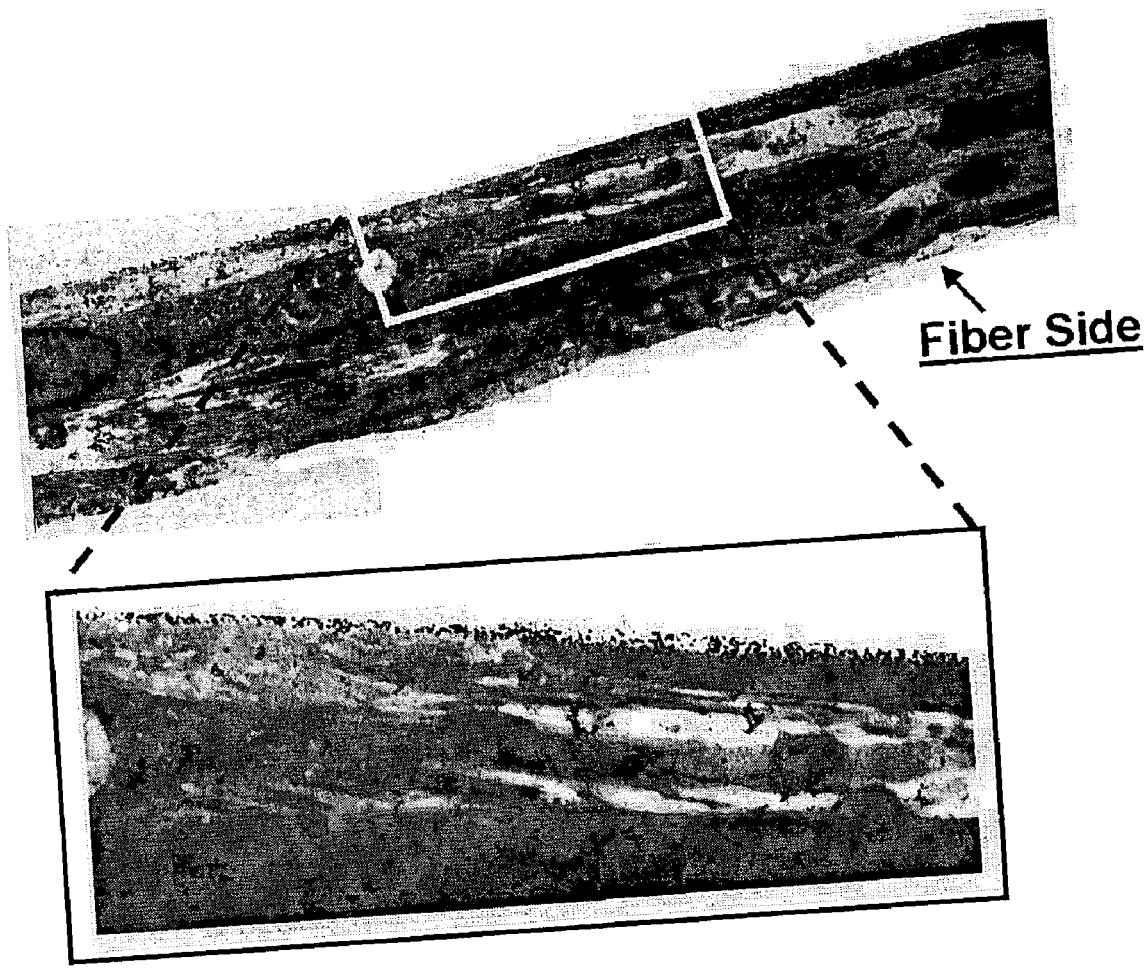

FIG. 21 shows a 7-0 single fiber construct cultured for 21 days; fibrillar deposits morphologically similar to that of collagen are present between cell layers (long arrows, magnification=1825×). In the inset, cellular interconnections are also seen between cell layers (short arrows, magnification=5,000×).

Figure 22:
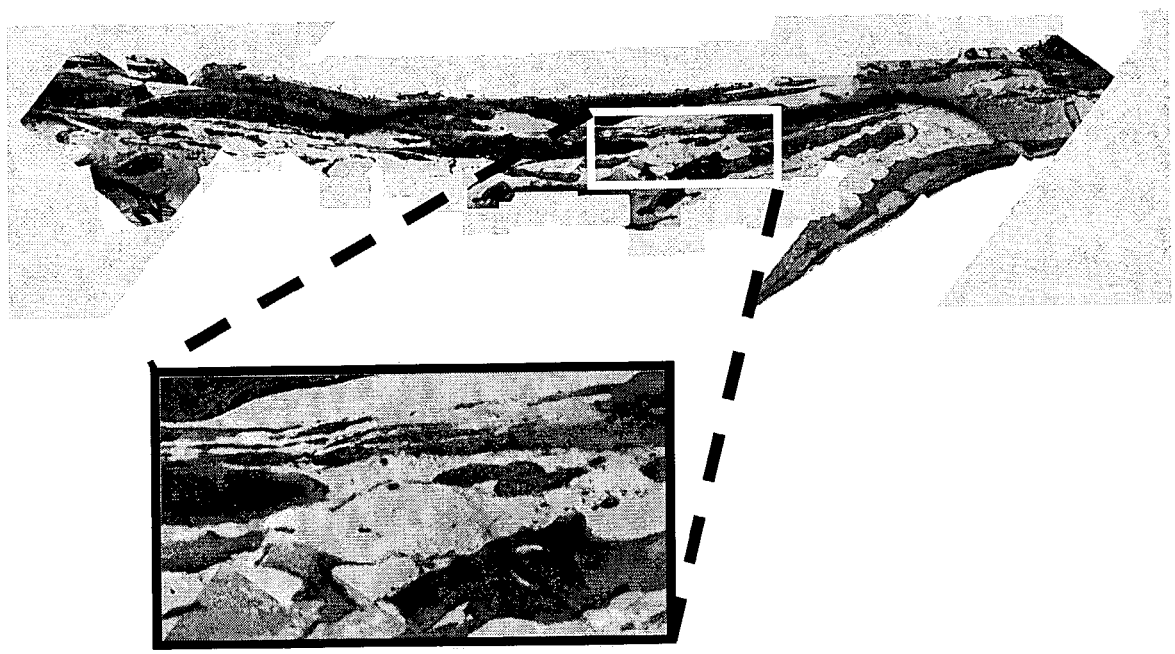

FIG. 22 shows a 7-0 25 micron spaced multi-fiber parallel array. Bridging between fibers shows cells that are multi-layered and seem to be less densely associated than that seen on a single 7-0 fiber (magnification 1000×). Inset shows flattened cells (long arrow) and cellular communication pseudo-pods are present as well (short arrows, magnification=7500×).

Figure 23:
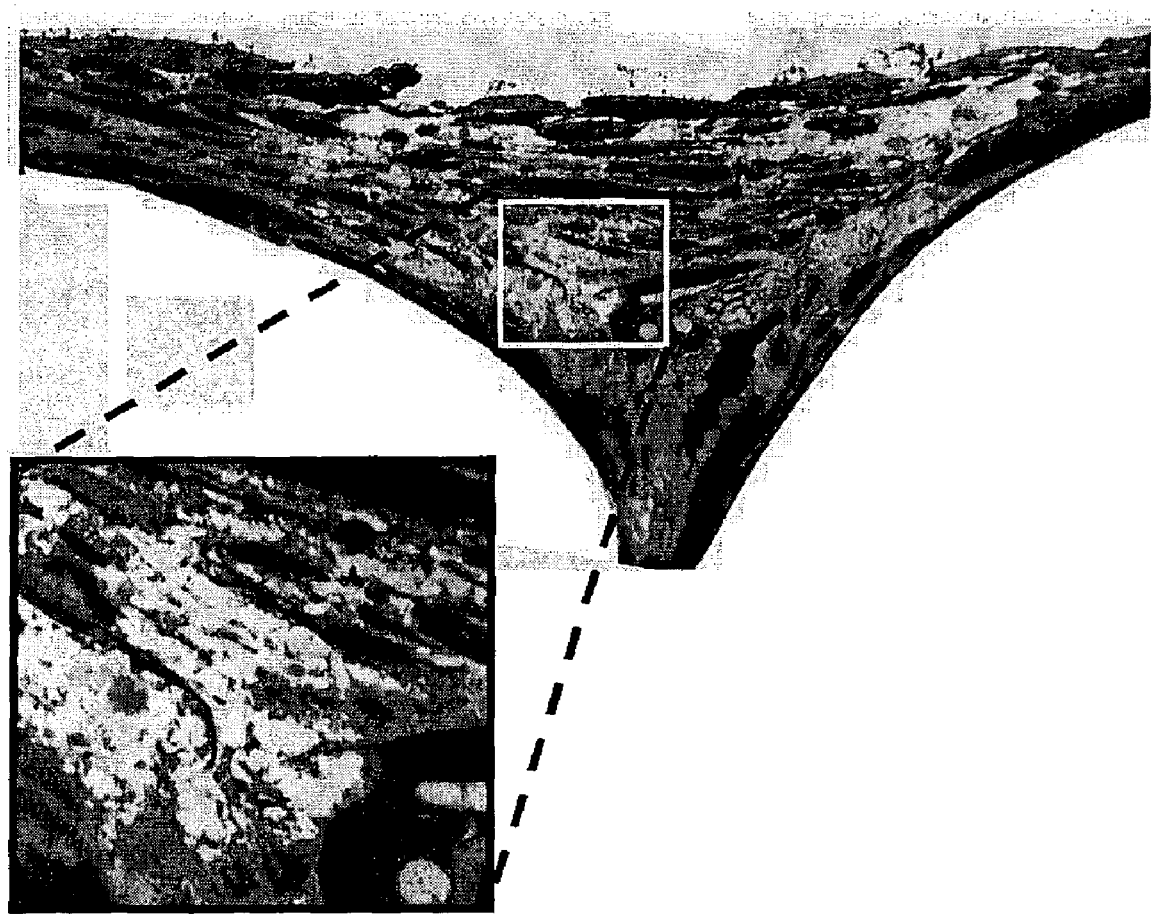

FIG. 23 shows a cross-sectional view of 7-0, 25 micron spaced parallel array that has been contracted, or had the fibers pulled together by the cells. Note the thickness of multi-layering particularly in the center of the image. There are also increased amounts of extra-cellular space vs. that see on the cells directly associated with the fibers (magnification 1000×). Inset shows ECM development between cells (magnification=4000×).

Figure 24:
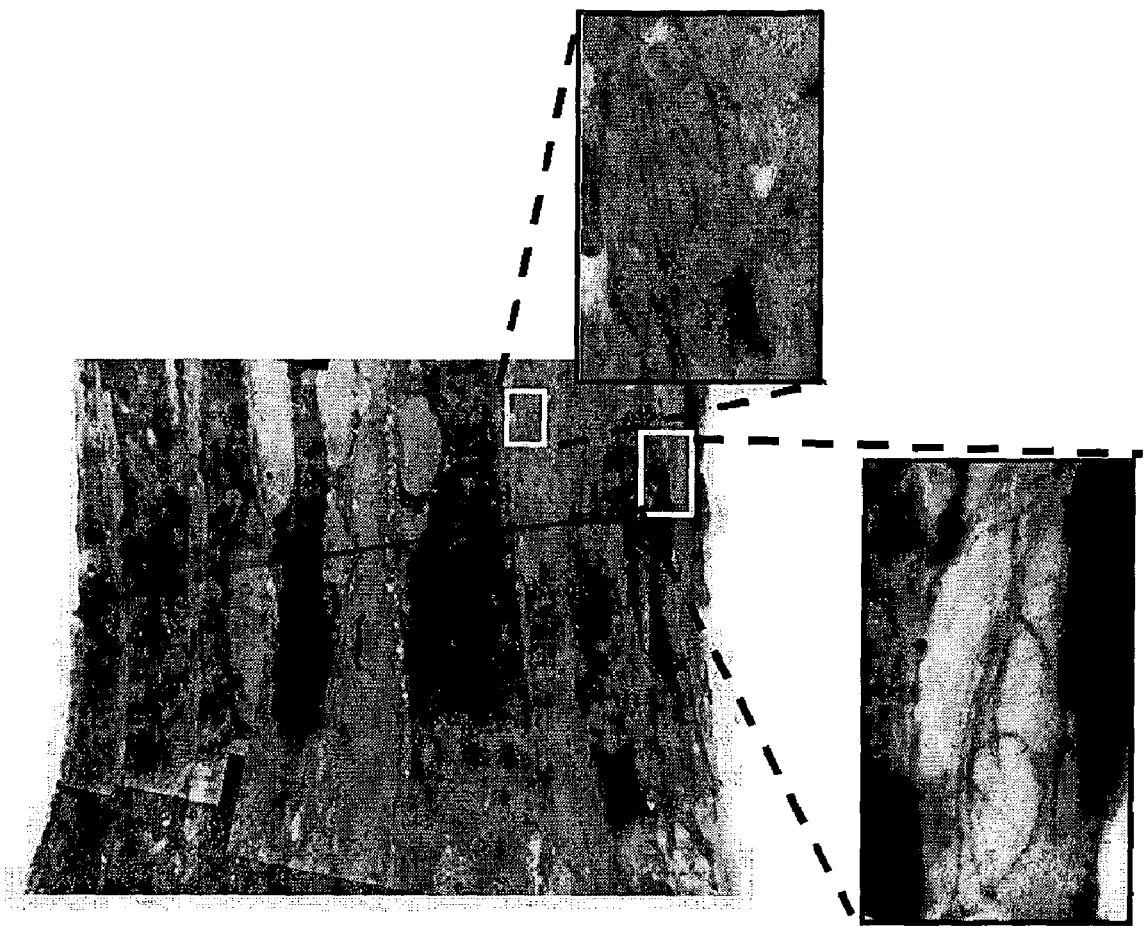

FIG. 24 shows TEM images of longitudinal section of the contracted portion of 7-0 25 micron spaced parallel array (magnification 1000×). Highly ordered cell layers are shown (short arrows). Oriented collagen fibrils are being deposited between layers (long arrows). Insets are higher magnification views of collagen fibrils (magnification=18,750×).

Figure 25:
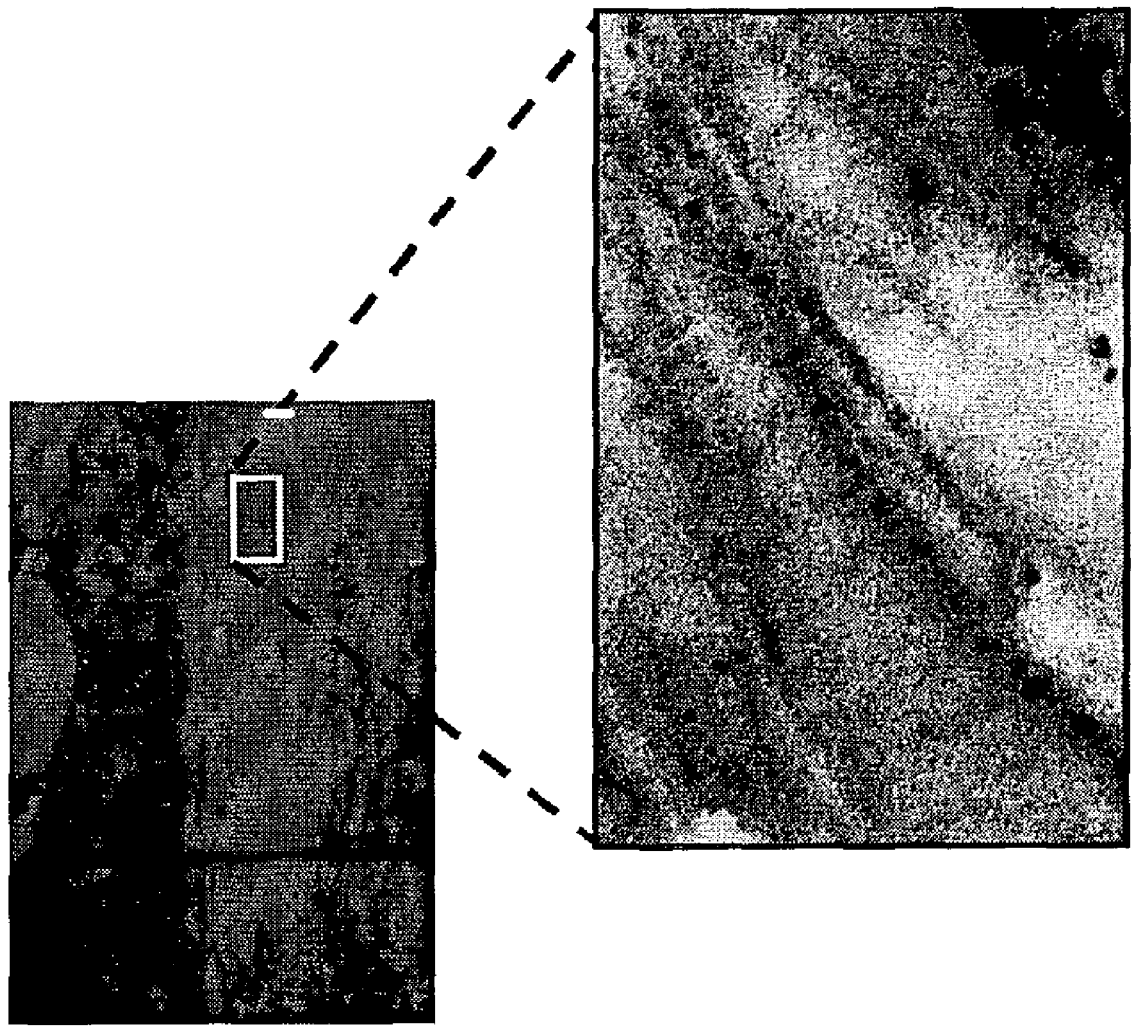

FIG. 25 shows collagen fibrils found in the extracellular space between cell layers (magnification of small image=1000×). Inset shows close up of collagen fibrils, which demonstrate the characteristic banding pattern widely associated with collagen.

Figure 26:
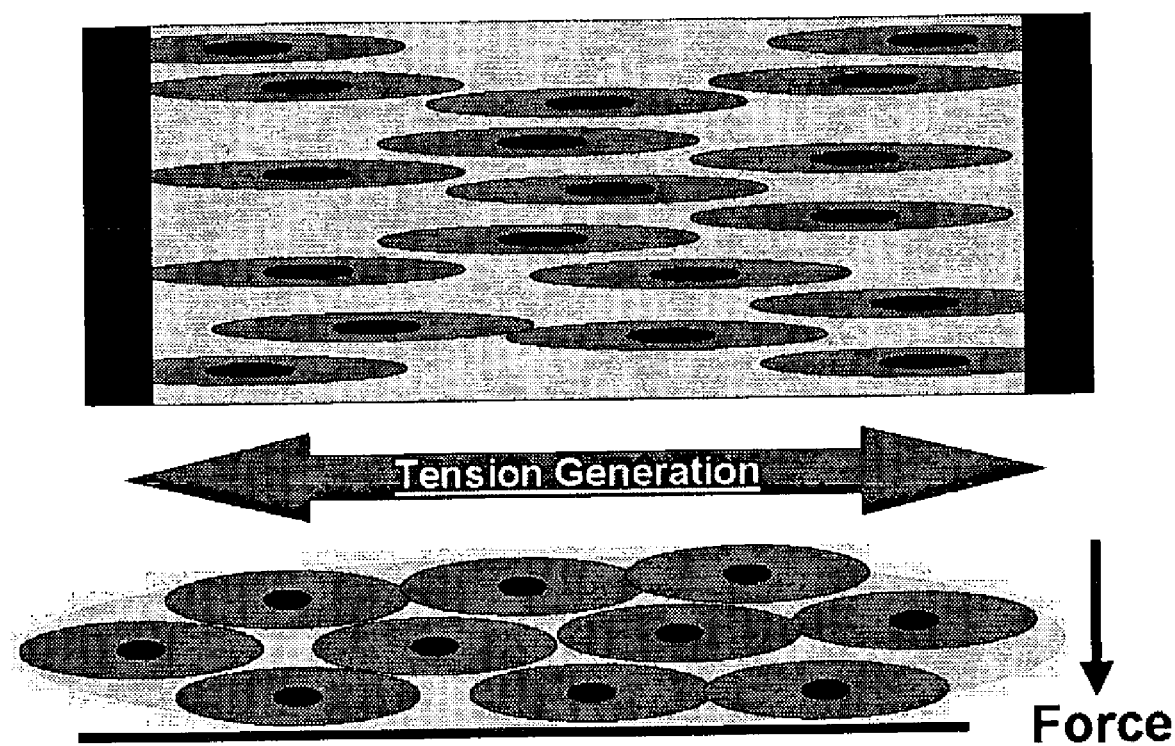

FIG. 26 shows the increased elongation of cells achieved within a multi-cellular bridge with increased amounts of available extracellular space. FIG. 26 also illustrates the effect of lateral tension generation which leads to compression of cells involved in the multi-layer. Note that the cells are not as elongated and there is not as much available extracellular space.

FIGS. 27A-27D show a micromanipulating apparatus of the subject invention that is useful for preparation of fiber constructs. FIG. 27A shows a microscope with micromanipulator on stage; note hanging weights attached to fibers by thread (arrow).

FIG. 27B shows a front-on view of micromanipulator showing handle and threads used to maintain tension on MAXON fibers. FIG. 27C shows an angled view of micromanipulator with pivot point shown. The pivot point was composed of silicone rubber, which the actual manipulator (30 gauge needle) was pushed through. FIG. 27D shows a front-on view of manipulator with polystyrene support ring and actual manipulator shown. Note MAXON fibers extending across the support ring under tension.

DETAILED DESCRIPTION

A method for producing a bioactive glass sol of the subject invention involves incorporating at least one biocompatible polymer. The polymer is a viscosity modifier which increases the viscosity range over which fibers can be sprayed or spun and broadens the time over which fibers can be sprayed or spun. A sol-gel process in accordance with the present invention is defined herein to be any process that includes the use of a sol-gel reaction in the preparation of a bioactive glass, such as that described by Oréfice, R L et al. (*Journal of Biomedical Materials Research*, Jun. 15, 2001, 55(4):460-467), which is incorporated herein by reference in its entirety.

As used herein, the term "bioactive glass" refers to those materials, including BIOGLASS® or polymer modified bioactive glasses such as those described herein, that "elicit a specific biological response at the interface of the material which results in the formation of a bond between the tissues and the material" (Hench, L. L., *Bioceramics: Materials Characteristics versus in vivo behavior*, ed. Annals of New York Academy of Sciences, 1988). Additionally, these materials act as both an osteoinductive and osteoconductive scaffold and promote tissue growth on, within, or adjacent to the material in vitro or in vivo via either a bonding or non-bonding mechanism. Therefore, they play an active role in both the mineralization of the tissue as well as function proactively in mediating cell function. A variety of sol gel derived bioactive glasses are known in the art and can be utilized with the subject invention.

Unless specified otherwise, the term "composition", as used herein, is inclusive of compositions and formulations prepared from the bioactive glass sol of the subject invention including, for example, bioactive glass fibers and bioactive glass fiber constructs, such as mats, meshes, and weaves. Methods of producing sol-derived bioactive glass fibers and mesh have been described previously (Domingues, R Z et al., *Journal of Biomedical Materials Research*, Jun. 15, 2001, 55(4):468-474; Oréfice, R L et al., *Journal of Biomedical Materials Research*, Jun. 15, 2001, 55(4):460-467). According to the subject invention, addition of a viscosity-modifying polymer during synthesis of the bioactive glass sol can be utilized in these methods to produce fibers and fibrous constructs.

A sol-gel process involves the evolution of inorganic networks through the formation of a colloidal suspension (sol) and gelation of the sol to form a network in a continuous phase (gel). The precursors for synthesizing these colloids include a metal or metalloid element surrounded by various reactive ligands. Metal alkoxides are the most popular sol-gel precursors because they react readily with water. The most widely used metal alkoxides are the alkoxysilanes, such as tetramethoxysilane (TMOS) and tetraethoxysilane (TEOS). However, non-alkoxysilane alkoxides such as aluminates, titanates, borates, calcium, titanium, zirconium, magnesium, iron, and potassium can also be used with the invention, either with or without an alkoxysilane.

Three reactions are generally used to describe the sol-gel process: hydrolysis, alcohol condensation, and water condensation. It should be understood that the characteristics and properties of a resulting sol-gel network can be controlled to an extent by those of ordinary skill in the art through manipulation of various parameters that affect the rate of hydrolysis and condensation reactions, such as pH, temperature, time of reaction, reagent concentrations, solvent type, purity, and concentration, catalyst nature and concentration, $H_2O$/alkoxide molar ratio, aging temperature and time, and drying.

Generally, the hydrolysis reaction, through the addition of water, replaces alkoxide groups (OR) with hydroxyl groups (OH). Subsequent condensation reactions involving the silanol groups (Si—OH) produce siloxane bonds (Si—O—Si), plus the bi-products of water or alcohol. Additionally, because water and alkoxides are immiscible, a mutual solvent is preferably utilized, such as an alcohol. In the presence of the alcohol, as a homogenizing agent, hydrolysis is facilitated due to miscibility of both the alkoxide and water. Catalysts can be used to further reduce this miscibility gap. As the number of siloxane bonds increase, the individual molecules become bridged and jointly aggregate in the sol. When the sol particles aggregate, or inter-knit into a network, a gel is formed. Upon a suitable drying process, trapped volatiles (water, alcohol, etc.) are driven off and the network shrinks as further condensation can occur.

When sols and gels are referred to herein as being "bioactive", such as in the phrases "bioactive glass sol" and "bioactive sol" and "bioactive sol-gel", it is understood that these compositions are considered in their dried states, absent solvents and catalysts, such as acid catalysts.

Preferably, the polymer is in solution with a diluent, such as ethanol (EtOH), and an acid catalyst, such hydrochloric acid. The viscosity modifying polymer solution preferably has an adjusted pH within the range of about 1 to about 7. The preferred pH of the viscosity modifying polymer solution will be a function of the particular viscosity modifying polymer utilized and the preferred method of processing, such as spraying, spinning casting, or coating.

The polymer solution can then be mixed with the alkoxide solution, such as by slowly adding the alkoxide mixture to the polymer solution, or vice versa, to form a mixture. At least one phosphorous source, such as TEP, and at least one calcium source, such as calcium chloride dihydrate, can be added to the mixture. The mixture is then further reacted to form a sol solution. Addition of one polymer solution may be added at any point in the reaction, such as prior to the hydrolysis of TEOS when the polymer is PVP. Phosphorous and calcium comprising molecules, such as TEP and calcium chloride are added sequentially following the hydrolysis reaction. One or more steps of the process of the invention can be repeated. Preferably, the pH of the resulting sol-gel solution containing the viscosity modifying polymer is about 1 to about 7. More preferably, the pH of the sol-gel solution is about 1.2 to 2, such as when the desired processing involves fiber spraying or spinning.

Upon aging, the sol-gel solution will form a gel, the initiation of which is delayed by the polymer present in the mixture. Upon a suitable drying process, such as vacuum drying without heat, or a mild heating (e.g., 150° C.), such as defined by the stability of the polymer, volatiles can be removed from the sol-gel solution without degrading the polymer component of the composition.

Various formulations, such as frits, monoliths, powders, coatings, fibers, sheets, mats, weaves, meshes, and composites, can be prepared from the bioactive glass sol of the invention. Preferably, fibers or fiber constructs, such as mats, meshes, or weaves, are prepared from the bioactive glass sol.

Fibers can be prepared from the bioactive glass sol using a variety of techniques, such as spraying, or extrusion through an orifice in a manner resembling wet or dry spinning or a combination of both. Preferably, an air spray technique is utilized to produce discontinuous fibers, and extrusion through a spinneret is utilized to yield continuous filaments. Viscosity of the sol can be monitored and adjusted through the removal of a solvent, such as ethanol, until a fibrous spray is achieved. Preferably, the viscosity of the bioactive glass spinnable sol is within the range of about 1.7 Pa sec. to about 3.0 Pa sec.

In addition to PVP, examples of polymers that can be used with the invention include, but are not limited to, polyethyleneimine (PEI), polycarboxylmethylcellulose (PCMC), polyethylenglycol (PEG), polypropylene oxide (PPO), polyvinylalcohol (PVA), polyacrylic acid (PAA), polymethylacrylic acid (PMAA), polystyrene sulfonic acid (PSSA), and gelatin. The viscosity modifying polymer utilized in the subject invention can also be a copolymer of, but not limited to, the aforementioned polymers (e.g., of random, alternating, or block type). The polymer can be a thermoplastic polymer, thermosetting polymer, or an elastomer.

Reaction parameters such as acid catalysis and reagent ratios can be adjusted to favor the formation of linear silica chains. The addition of the viscosity modifying polymer during production of the bioactive glass sol, in accordance with the subject invention, provides a material which is more easily sprayed or spun into fibers.

The BG fibers of the invention have also been shown to exhibit in vitro bioactivity and influence cell growth in culture. The nature of the fibers is such that diameters along with porosity and spacing between fibers can be tailored, making them attractable for use as implantable materials for tissue engineering. A decrease in the spacing between the fibers has been shown to result in enhanced proliferation of the cells. Adjustment of the porosity can thus be fixed to provide sufficient space for the influx of cells, blood vessels and metabolic exchanges characteristic of native bone, while at the same time allowing for a large population of cells to infiltrate and integrate within the implant.

As described in Examples 3 and 4, a 77S bioactive glass sol composite was successfully synthesized following a sol gel process through the incorporation of polyvinylpyrrolidone (PVP). The resulting material was in turn sprayed to yield short, discontinuous fibers. The addition of the polymer to the BG sol greatly facilitated the spraying process, allowing for enhanced control of the rheological properties and prolonged spraying times through impedance of gelation. The fibrous spray was in turn more homogeneous in nature than BG sols alone. The BG composite fibers were shown to be bioactive and enhance cellular proliferation. Decreasing the porosity of the fibrous scaffolds led to an increase in the proliferation of rat MSCs preceding differentiation. These scaffolds have the potential to direct and mediate cell growth as tissue engineering constructs in bone regeneration.

In one embodiment, the bioactive glass material according to the invention has a composition comprising (by percent weight) of 0-70% $SiO_2$, 0-40% CaO, 0-40% $Na_2O$, 0-40% $K_2O$, and 0-20% $P_2O_5$. An exemplary composition of bioactive glass has a composition comprising (by percent weight) of 40-60% $SiO_2$, 10-30% CaO, 10-35% $Na_2O$, 2-8% $P_2O_5$, 0-25% $CaF_2$, and 0-10% $Ba_2O_3$. In another exemplary embodiment, the bioactive glass formulation is (by percent weight) 45% $SiO_2$, 24.5% CaO, 24.5% $Na_2O$, and 6% $P_2O_5$.

In yet another embodiment, the bioactive glass formulation (by percent weight) is 45% $SiO_2$, 35% CaO, 15% $K_2O$ and 5% $P_2O_5$. Any of the bioactive glass formulations can, optionally contain minor elements such as MgO, ZnO, $B_2O_3$, $Al_2O_3$ and MnO at a concentration of 0-5%.

Sol gel glasses generally comprise >60% $SiO_2$, 0-40% CaO, and 0-20% $P_2O_5$ (generally 4% $P_2O_5$), all expressed in mole percents. $CaF_2$ can also be used in place or in combination with CaO.

The composition of the invention can be applied as a film or coating on a substrate. The substrate can be composed of any material, such as metal, polymer, and/or ceramic materials (such as hip joints, knee joints, dental implants, spinal fusion cages, and bone fillers).

Fibrous compositions of the subject invention can be woven or unwoven, and can comprise single or multiple fibers in various orientations, having various porosities, and the fibers can be spaced apart from one another various distances. For example, as described in Example 4, it has been determined that the rate of proliferation and the total number of cells were found to depend on both the porosity of the composition (in this case, a fiber construct) and the time in culture. The concentration of cells was shown to increase as the spacing between the fibers decreased. As shown in FIG. 8, cells seeded on the fiber constructs exhibited an increase in proliferation with a decrease in porosity. In particular, for applications in which growth of cells on or within the fibrous compositions of the subject invention is desired in vitro or in vivo, the porosity (fiber volume divided by the construct volume) of the composition is preferably within the range of about 70% and about 100%. Additional packing of fibers into the fibrous compositions results in shorter spacing between adjacent fibers as well as an increase in available surface area. Closer packing of the fibers allows the cells to bridge the gaps between the fibers, resulting in less compaction and prolonged differentiation. In contrast, as described in Example 4 with regard to stem cells, dispersion of fibers allows for an expansion in available space for cell growth coupled with the preservation of cells in an undifferentiated state leads to increased proliferation for extended periods.

Thus, by manipulating the architectural features of the compositions of the subject invention, such as fiber diameter, spacing, orientation, and porosity, cells that are applied to or incorporated within the compositions can be directed to behave in predictable ways. In particular, cells of mesenchymal origin, such as fibroblasts and osteoblasts, the latter being the primary bone forming cells in mammals, can be induced to orient themselves along parallel features, such as grooves. Once oriented, osteoblasts and osteoblast-like cells will mineralize and lay down extra-cellular matrix (ECM) parallel to microtopographical features on the compositions of the invention. Using the phenomena of contact guidance, which orients not only cells, but cell products (such as ECM), the compositions of the subject invention can be designed as substrates or scaffold materials for cells.

Bioactive glass fibers of the subject invention can be woven into mats and the tightness and geometry of the weave, as well as the diameter of the fibers, allow a number of control features. Fiber based scaffolds can be designed to allow for initial nutrient exchange, as well as longer term vascular infiltration. In addition, the direction of cellular growth and ECM deposition can be influenced so that a decreased remodeling requirement is present after the newly created tissue is formed. For example, cells can be aligned to a degree that approximates the alignment and orientation they will exhibit after remodeling and so will be less distant from their equilibrium state. Proper spacing of fibers is desired to allow optimal cell tension and stretch, but it should also be optimized for the aggregate activity, or cooperative bridging of cells occurring across gaps in the scaffold.

Generally, as the diameter of fibers decrease, cell growth and elongation along the length of the fibers increase. For example, using the spraying techniques utilized in the Examples, fibers from about 1 μm to about 40 μm in diameter and about 0.5 mm to about 2 mm in length were produced. Fibers can also produced using a spinnerette, for example. Preferably, for cell growth along the length of the fibers, the diameter of the fibers are less than about 100 μm. More preferably, the fibers have a diameter within the range of about 10 μm to about 50 μm.

The present invention also includes a method of treating a patient having a hard tissue or soft tissue defect by applying a bioactive glass composition described herein to the site of the defect, thereby promoting repair of the tissue defect. As used herein, the term "patient" refers to any human or non-human animal having a hard tissue or soft tissue defect. According to the method of the subject invention, a therapeutically effective amount of the composition can be applied at the site of a defect to partially or fully restore structural integrity and functional ability to the tissue.

Once applied, the composition of the subject invention can function as a filler (or partial filler) or plug, to mend the defect. The amount to be applied will depend upon the size and nature of the defect, and the clinical outcome that is sought. The composition can be applied in a malleable form, for example, in conjunction with a polymer gel or matrix, as a paste or putty, such that the administered composition takes the shape of the defect. Alternatively, the composition can be molded or pre-cast into a desired shape (such as the shape of the defect) using composite molding methods known to those of ordinary skill in the art, and the molded composition can be administered as a solid or semi-solid article. Thus, the size, volume, thickness, and shape of the molded article can be controlled, as desired. According to the method of the subject invention, the composition can be applied so that it directly contacts existing bone adjacent to, or defining, a bone defect site, or the composition can be contacting another implant, or both.

The composition of the subject invention can be applied to the tissue defect site as a solid or liquid. Regarding liquid applications, once applied with a syringe for example, the liquid composition can coagulate or cure ("set") shortly after application to form a solid.

The composition of the subject invention can be used as a vehicle for the in situ delivery of biologically active agents. The biologically active agents incorporated into, or included as an additive within, such as encapsulated by compositions according to the invention. Thus, the biologically active agent composition of the subject invention can include, without limitation, medicaments, vitamins, mineral supplements, cells, growth factors, substances used for the treatment, prevention, diagnosis, cure or mitigation of disease or illness, substances which affect the structure or function of the body, or drugs. The biologically active agents can be used, for example, to facilitate implantation of the composition into a patient and to promote subsequent integration and healing processes. The active agents include, but are not limited to, antifungal agents, antibacterial agents, anti-viral agents, antiparasitic agents, growth factors, angiogenic factors, anaesthetics, mucopolysaccharides, metals, cells, and other wound healing agents. Because the processing conditions can be relatively benign (physiological temperature and pH), live cells can be incorporated into the composition during its formation, or subsequently allowed to infiltrate the composite through tissue engineering techniques.

The compositions of the subject invention can be applied to hard tissue or soft tissue of a patient in isolation, or the compositions can be applied to, or formulated with, other materials for implantation into a patient. For example, the compositions of the subject invention can be applied in a woven form for bone treatment.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Although the compositions of the subject invention can optionally include cell growth promoting agents, in one embodiment, the composition of the subject invention does not include cell growth promoting agents, such as bone morphogenic agents (BMPs). BMPs, such as certain members of the TGF-β family, mediate developmental processes including morphogenesis, differentiation, cell survival and apoptosis. BMPs are known to promote bone regrowth. In a further embodiment, the composition of the subject invention includes cells, such as mesenchymal stem cells, and does not include any cell growth promoting agents, such as BMPs. The compositions of the subject invention are capable of supporting the growth of cells in the absence of cell growth promoting agents.

Growth factors that can be incorporated into the composition of the present invention include, but are not limited to, basic fibroblast growth factor (bFGF), acidic fibroblast growth factor (aFGF), nerve growth factor (NGF), epidermal growth factor (EGF), insulin-like growth factors 1 and 2 (IGF-1 and IGF-2), platelet-derived growth factor (PDGF), tumor angiogenesis factor (TAF), vascular endothelial growth factor (VEGF), corticotropin releasing factor (CRF), transforming growth factors alpha and beta (TGF-α and TGF-β), interleukin-8 (IL-8), granulocyte-macrophage colony stimulating factor (GM-CSF), the interleukins, and the interferons.

Cells that can be applied onto the compositions of the subject invention (e.g., seeded), or incorporated into the compositions of the subject invention, can range in plasticity from totipotent or pluripotent stem cells (e.g., adult or embryonic), precursor or progenitor cells, to highly specialized or mature cells, such osteocytes. Stem cells can be obtained from a variety of sources, including fetal tissue, adult tissue, cord cell blood, peripheral blood, bone marrow, and brain, for example. Stem cells, such as mesenchymal stem cells, and non-stem cells (e.g., specialized or mature cells, and precursor or progenitor cells) can be differentiated, expanded, and/or genetically modified before, during, or after addition to the compositions of the subject invention.

Methods and markers commonly used to identify stem cells and to characterize differentiated cell types are described in the scientific literature (e.g., Stem Cells: Scientific Progress and Future Research Directions, Appendix E1-E5, report prepared by the National Institutes of Health, June, 2001). The list of adult tissues reported to contain stem cells is growing and includes bone marrow, peripheral blood, brain, spinal cord, dental pulp, blood vessels, skeletal muscle, epithelia of the skin and digestive system, cornea, retina, liver, and pancreas.

Other agents that can be incorporated into the composition of the invention include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins that can be incorporated into, or included as an additive within, the composition of the subject invention include, but are not limited to, collagen (including cross-linked collagen), fibronectin, laminin, elastin (including cross-linked elastin), osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor, or combinations and fragments thereof. Other proteins associated with other parts of human or other mammalian anatomy can be incorporated or included as an additive, include proteins associated with cartilage, such as chondrocalcining protein, proteins associated with dentin, such as phosphoryin, glycoproteins and other Gla proteins, or proteins associated with enamel, such as amelognin and enamelin. Agents incorporated into the composition of the subject invention may or may not facilitate or enhance osteoinduction. Adjuvants that enhance an immune response can also be used in conjunction with the composition of the subject invention.

The biologically active agents can first be encapsulated into microcapsules, microspheres, microparticles, microfibers, within sol gel matrices, reinforcing fibers and the like to facilitate mixing and achieving controlled, extended, delayed and/or sustained release. Encapsulating the biologically active agent can also protect the agent against degradation during formation of the composition of the invention. The biological agents can also be adsorbed onto the surface of the BG fibers or chemically attached to their surface.

In a preferred embodiment of the invention, the biologically active agent is controllably released into a mammal when the composition of the invention is implanted into a mammal. Preferably, the composition of the subject invention is used to replace or span an area of discontinuity in the hard or soft tissue in the mammalian body, acting as a scaffold for the regrowth of new tissue. In this context, the term scaffold is meant to indicate the structure that can be significantly remodeled by the biological processes or partially or completely resorbed. The area of discontinuity in the tissue can be as a result of trauma, disease, genetic defect, or surgery, for example.

The composition of the subject invention can be formulated into a variety of shapes suitable for its function. For example, where the composition is intended as a bone graft substitute, a plate, pin, rod, screw, anchor, tack, arrow, staple, button, or other regular or irregular shape is appropriate.

The subject invention also includes methods of repairing hard and soft tissue defects by applying the bioactive fibers of the subject invention to the defect site on the patient. The term "tissue defect", as used herein, refers to any tissue deficient region, such as a void, gap, recess, fracture, or other discontinuity in the hard or soft tissue. Examples of hard tissue include, but are not limited to, bone, dentin, and enamel. Examples of soft tissue include, but are not limited to, skin, blood vessels, and oral mucosa. The tissue defect can be artificially or naturally established, and can occur due to disease or trauma, for example. Thus, the defect can occur as a consequence of pathologic, inflammatory, or tumor diseases, surgical interventions, or bone fractures, and the like. For example, in the case of certain diseases, such as bone tumors, the bone defect is artificially established by removing the tumor tissue. Thus, according to the method of the subject invention, the composition can be applied, for example, to repair hard tissue defects such as periodontal defects, for craniofacial reconstruction, joint reconstruction, fracture repair, to conduct orthopedic surgical procedures, and spinal fusion, for example.

The compositions of the invention can be applied to the surface(s) of, or integrated within, a variety of medical devices intended for implantation into a patient, such as prosthetic devices. The underlying structure of the device may be any desired design. Such devices can be implanted into hard tissue, such as bone, or soft tissue, such as in or about the vasculature of a patient. For example, the compositions of the subject invention can be applied to or incorporated within stents (e.g., vascular stents), catheters, grafts (e.g., vascular grafts), stent grafts, synthetic bypass grafts, biliary stents, ureteral stents, aneurysm filling coils and other coiled devices, implantable vascular access ports, trans myocardial revascularization ("TMR") devices, percutaneous myocardial revascularization ("PMR") devices, pumps, filters, valves, and artificial organs. The medical device, or portion of the medical device, to be coated or otherwise integrate the composition of the subject invention, can be made of metal, polymeric materials, ceramics, composites, or combinations thereof. Examples of metallic surfaces include, but are not limited to those composed of surgical grade metals, stainless steel, nickel, titanium, aluminum, copper, gold, silver, platinum and combinations thereof. The compositions of the subject invention can also be applied to, or otherwise be incorporated into, sutures, bone anchors, bone screws, protective platings, hip and joint implants, electrical leads, biosensors, and probes.

EXAMPLES

It should be understood that the examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof.

Example 1

Sol Gel Synthesis

A 77S bioactive glass sol was synthesized from tetraethoxysilane (TEOS), triethylphosphate (TEP), and calcium chloride dihydrate. All reagents were used as received from ALDRICH (Sigma-Aldrich Fine Chemicals, Milwaukee, Wis. 53201). Initially, DI $H_2O$ was adjusted to a pH of 1.6 using 12N HCl. A 5% weight solution of PVP, $M_n=1\times10^6$ g/mol, was diluted in ethanol. The volume of the PVP solution added was approximately 1% of the final volume of the sol. Both the $H_2O$/HCl and PVP/EtOH solutions were stirred for 10 minutes each, after which point they were combined and stirred for an additional 5 minutes. TEOS was then slowly added to the mixture and subsequently hydrolyzed for 60 minutes. The ratio of TEOS:$H_2O$:EtOH was fixed at 1:2:4 (Oréfice, R L et al., *Journal of Biomedical Materials Research*, Jun. 15, 2001, 55(4):460-467; Domingues, R Z et al., *Journal of Biomedical Materials Research*, Jun. 15, 2001, 55(4):468-474). TEP and $CaCl_2 \cdot 2H_2O$ were then added sequentially, with each reagent requiring a 60 minute reaction period. Temperature and pH variations throughout the course of the reaction were monitored using an EA 920 Expandable Ion Analyzer from Orion Research.

Figure 1:
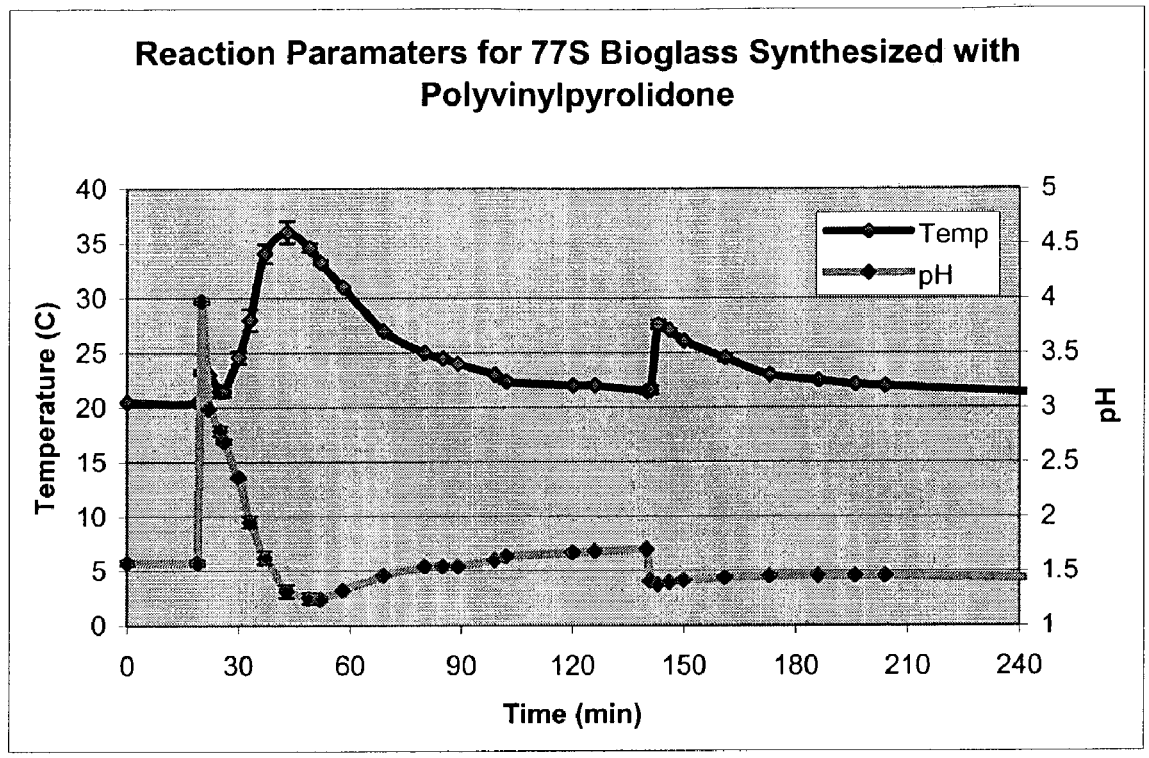

The thermodynamic variations in temperature and pH through the course of the reaction described above are illustrated in FIG. 1. The use of an acid catalyst and the ratio of $H_2O$:TEOS (r value) were adjusted to favor the formation of linear silica chains that would in turn allow for fiber spinning (Oréfice, R L et al., *Journal of Biomedical Materials Research*, Jun. 15, 2001, 55(4):460-467; Domingues, R Z et al., *Journal of Biomedical Materials Research*, Jun. 15, 2001, 55(4):468-474; Brinker, C J and Scherer, G W. Sol-gel science: The physics and chemistry of sol-gel processing. San Diego: Academic Press; 1990). Initially the pH of DI water was adjusted to 1.6 using 12N HCl. Acid catalysts in sol gel reactions favor the formation of weakly branched extended structures more suitable for spinning than sols synthesized with a basic catalyst, which result in the formation of particles and clusters. An acid catalyst also results in a slow condensation rate, allowing one to greatly enhance the viscosity through solvent removal without premature transformation of the sol into a gel (Brinker, C J and Scherer, G W. Sol-gel science: The physics and chemistry of sol-gel processing. San Diego: Academic Press; 1990). Adjustment of the r value to 1:2 further favors the formation of a linear network suitable for spinning through the theoretical hydrolysis of two of the four functional ethoxy groups on the TEOS molecule.

Addition of PVP to the BG sol during synthesis resulted in a two phase phenomena. The addition of small amounts of PVP results in a clouding of the solution followed by an aggregation of the majority of the precipitate. Continued stirring of the sol did not result in resolubization. As the amount of PVP added to the sol was increased a different mechanism was observed. Initially the sol would become cloudy; however, continued stirring resulted in an aggregation of the precipitate followed by dissolution back into solution.

Polyvinylpyrrolidone was observed to be individually soluble in ethanol, TEOS, and water. The hydration of TEOS however led to the formation of a precipitate, indicating insolubility of PVP in the intermediate structure containing silanol and ethoxy groups. For these low PVP concentration solutions the precipitate failed to redissolve. The polymer acted as a flocculation agent, resulting in the aggregation of the TEOS intermediates and their subsequent precipitation (Otsubo, Y. Rheology of colloidal suspensions flocculated by reversible bridging. *Chemical Engineering Science*. 2001. V 56, p 2939-2946; Agren, P; Rosenholm, J B. Phase Behavior and structural changes in TEOS derived gels in the presence of polyethylene glycol studied by Theological techniques and visual observation. *Journal of Colloid and Interface Science*. 1998. V 204, p 45-52). The amount of the polymer was insufficient to completely coat the forming silica chains and in turn led to the entrapment of the TEOS intermediate within the loops and tails of the polymer chain and subsequent precipitation (Biggs, S; Habgood, M; Jameson, G J, Yan, Y. Aggregate structures formed via a bridging flocculation mechanism. Chemical Engineering Journal. 2000. V 80, p 13-22).

As the amount of PVP added was increased the resulting precipitate was short lived. Continued stirring led to the return of the aggregate to solution after approximately 10 minutes. Those sols without precipitate were observed to remain in the solution state much longer than BG sols synthesized without PVP, as shown by the viscosity profile shown in FIG. 10 which demonstrates sol stability for about 120 days (4 months). Thus, gelation was prolonged for 4 months in quiescent samples, whereas those synthesized without PVP were found to gel within 2-3 weeks. Increasing the amount of PVP led to steric stabilization of the sol and enhanced the shelf life.

Example 2

Fiber Synthesis and Characterization

Fibers were produced from bioactive sol compositions according to the invention using an air spray technique. Prior to spraying, the viscosity of the filtered sol was adjusted through the removal of EtOH, initially at 80° C. and then under partial vacuum. Viscosities were monitored using a Brookfield DV11 Digital Viscometer. When the sol viscosity reached approximately 2 Pa sec it was examined for its ability to yield fibers when spayed. If the sprayed material was still particulate in nature further solvent was removed until a fibrous spray was observed. Upper viscosity limits for a spinnable sol was found to approach 3 Pa sec. Fiber spraying was performed using a Badger Air Brush gun with $N_2$ at a pressure of 50 psi. Fibers were sprayed onto a polypropylene surface with surrounding air-flow from approximately 1.5 meters. After spraying the fibers were air dried overnight and then sintered at 900° C. for 3 hours, pyrolizing the PVP. Morphological examination of the fibers was performed using both optical and scanning electron (JEOL 6400) microscopies. Thermal analysis using a Seiko TG/DTA 220C was performed on undried fibers in order to monitor the transitions and mass loss that occurred during sintering.

Figure 3A:
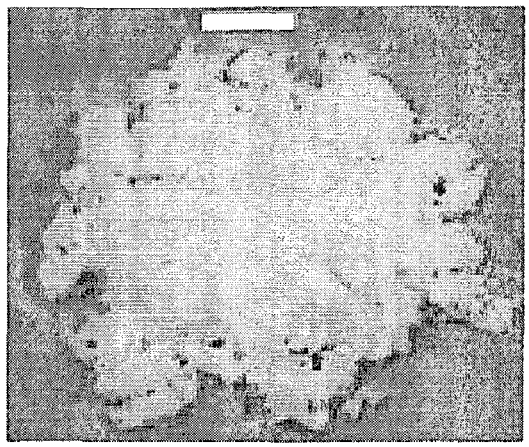
Figure 3B:
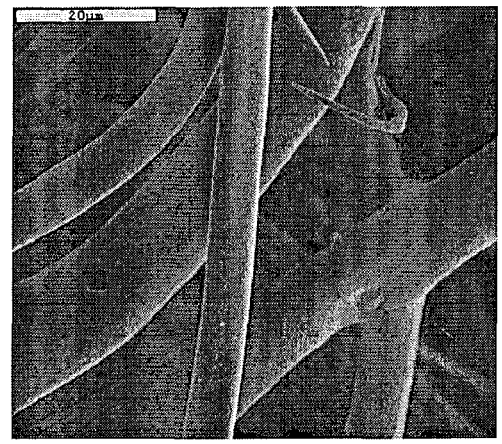

FIGS. 3A and 3B show images of sprayed 77S bioactive glass fibers synthesized with PVP as described above. FIG. 3A shows an optical image (SB=2 cm) while FIG. 3B shows a 1300×SEM image.

Figure 2:
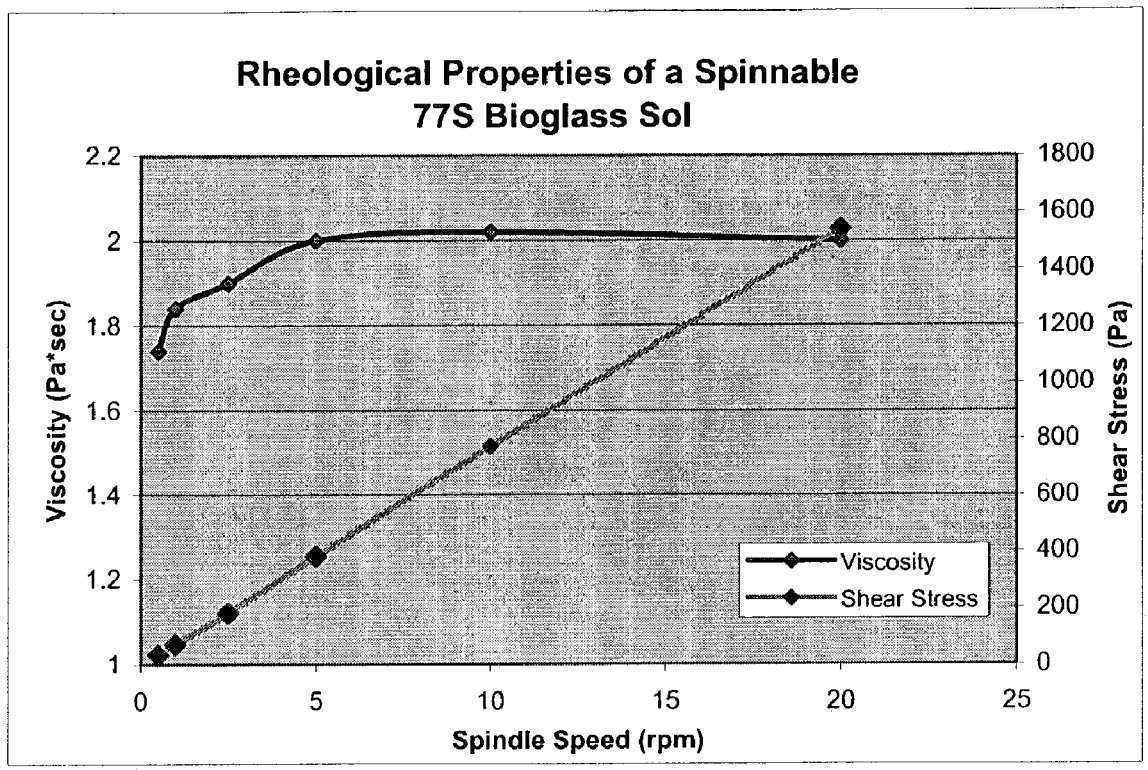
Figure 3C:
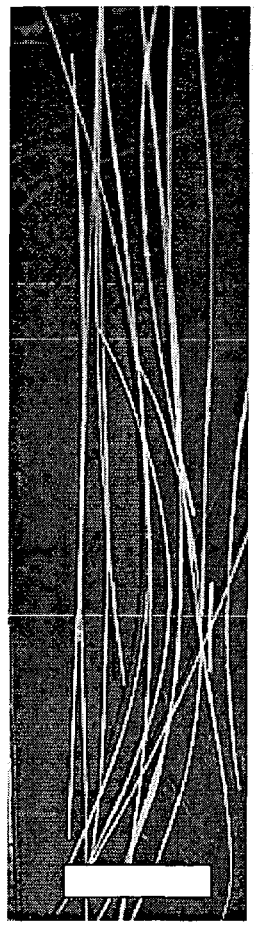
Figure 3D:
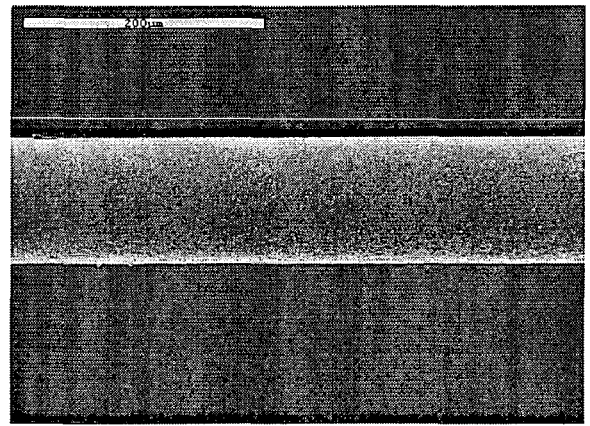

Also, continuous 77S bioactive glass fibers were formed by extrusion through a spineret. FIG. 2 shows the viscosity profile for a sprayable 77S bioactive glass sol synthesized with PVP. FIGS. 3C and 3D show images of spun 77S bioactive glass fibers synthesized with PVP. FIG. 3C shows an optical image (SB=1 cm) while FIG. 3D shows a 250×SEM image.

The addition of PVP to the BG sol was found to greatly facilitated the spraying process. Previous synthesis of a BG sol without the incorporation of PVP led to a material which was often difficult to spray into fibers due to the rapid sol to gel transition. The range of acceptable spraying viscosities was closely mirrored by the transition of the sol to a gel, and as the material approached viscosities near those suitable for spraying the sol would often gel. Isolation of a sol suitable for spraying was therefore difficult to achieve due to the rapid transition in the viscosity range of interest. Addition of PVP allowed for enhanced control of the rheological properties without having to precisely isolate the sol just prior to its transformation into a gel. Modulation of the sol viscosity in this manner thus broadened the region over which the material could be sprayed into fibers.

In addition to the incorporation of PVP, precise control of solvent removal also allowed for increased control of the rheological behavior of the sol. When solvent was removed in a slow and mediated manner from the BG sol, the resulting material was most often a Newtonian like fluid. Those sols without PVP or when solvent removal was carried out in a more rapid manner often yielded a psuedoplastic fluid. The Newtonian fluid was sprayed into fibers much more easily than the shear thinning fluid, most likely due to its ability to maintain the integrity of the silica network when subjected to the high shearing forces of the spraying process. The Newtonian like sol containing PVP resulted in a highly homogeneous distribution of fibers, with less particulate material than was observed in a shear thinning or BG sol alone. Thus mediation of the viscosity through PVP addition yielded a sprayable material that led to an increase in the efficiency of fiber production. SEM analysis of fibers gave a mean diameter of 9.37±5.34 µm (n=53). A viscosity profile of a sprayable sol as well as micrographs of the sprayed fibers are illustrated in FIGS. 2 and 3, respectively.

Figure 4:
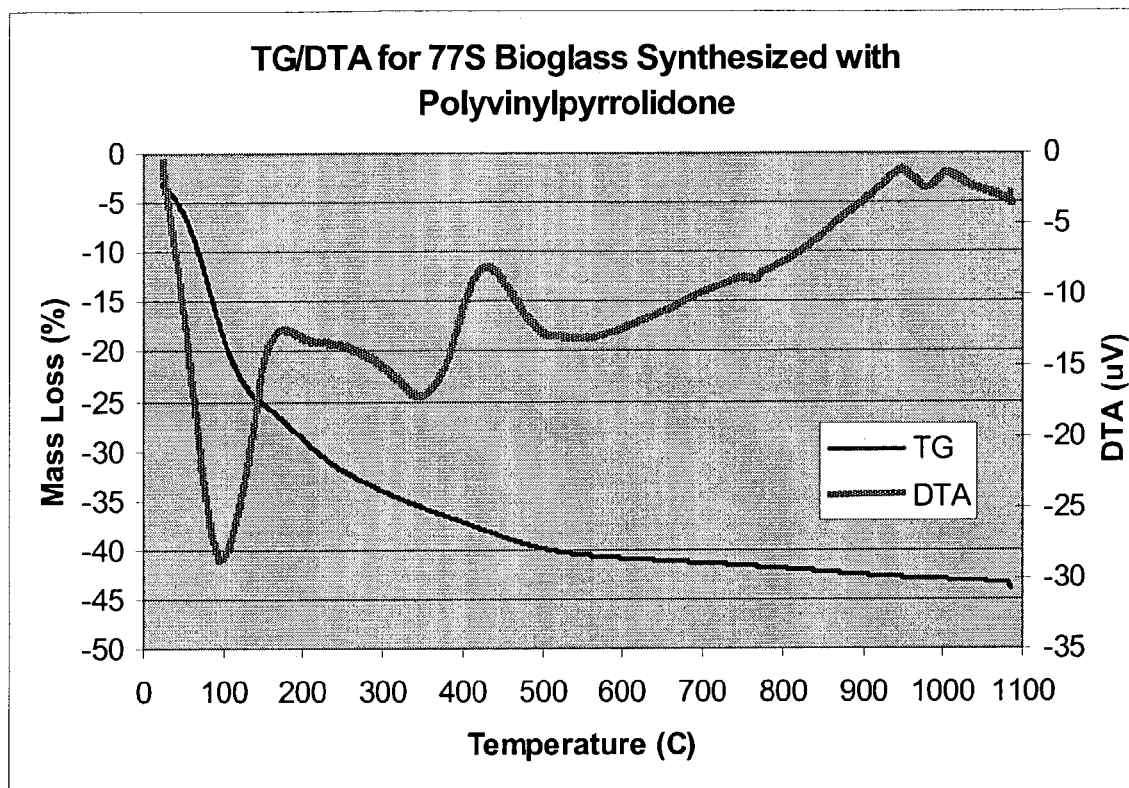
Figure 5A:
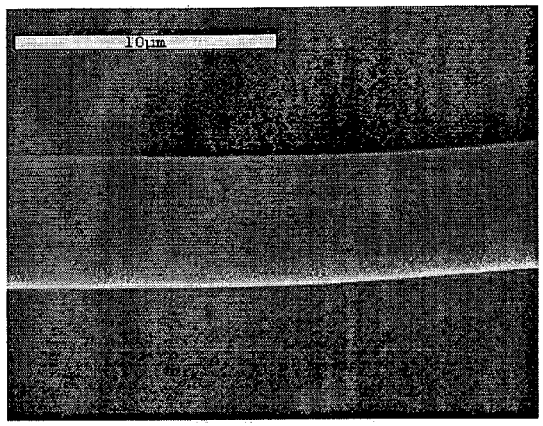
Figure 5B:
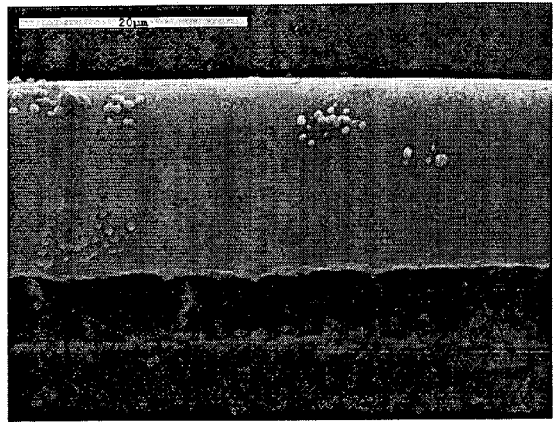
Figure 5C:
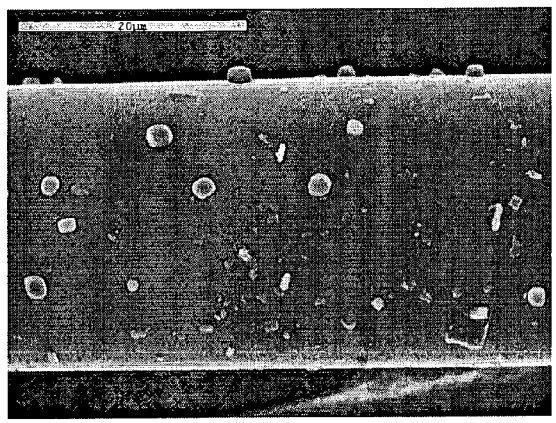
Figure 5D:
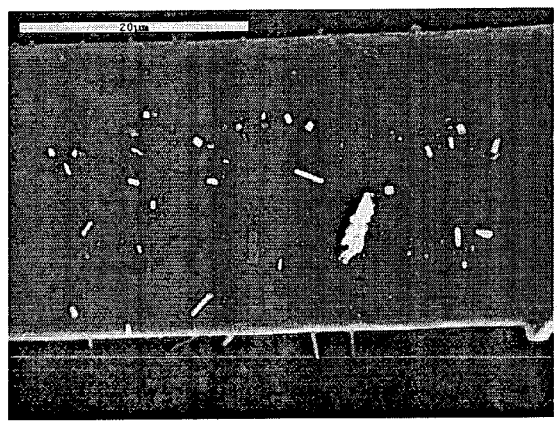
Figure 5E:
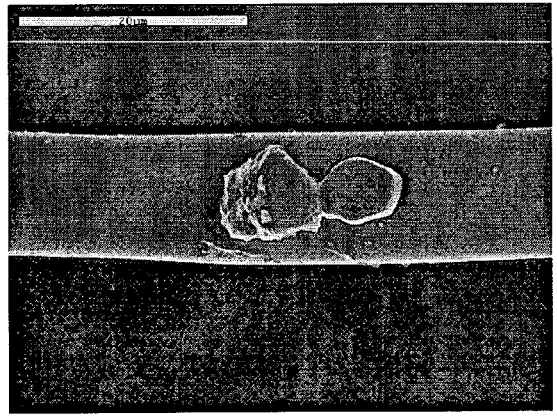
Figure 5F:
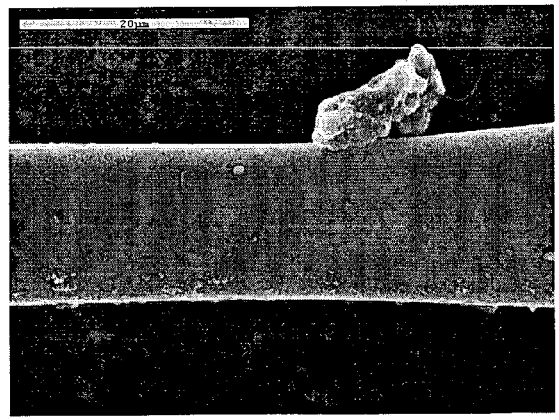
Figure 6A:
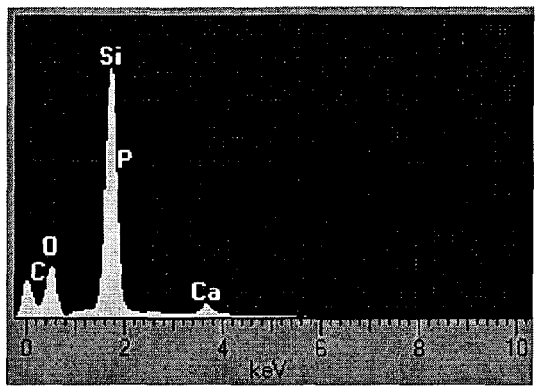
FIGS. 6A-6F show EDX Spectra of fibers (FIG. 6A) and crystals (FIGS. 6B-6F) seen in SEM images in FIG. 5.
Figure 6B:
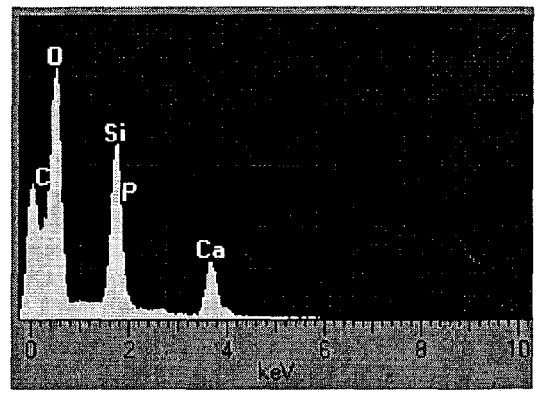
Figure 6C:
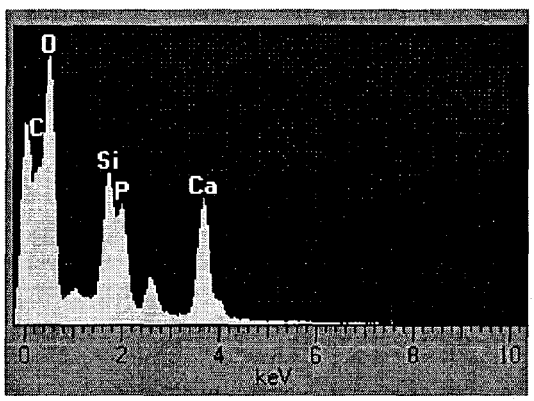
Figure 6D:
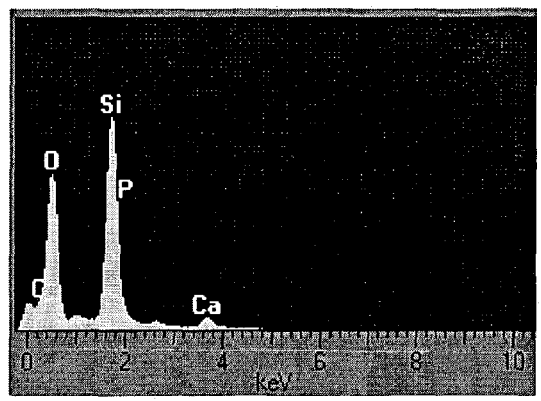
Figure 6E:
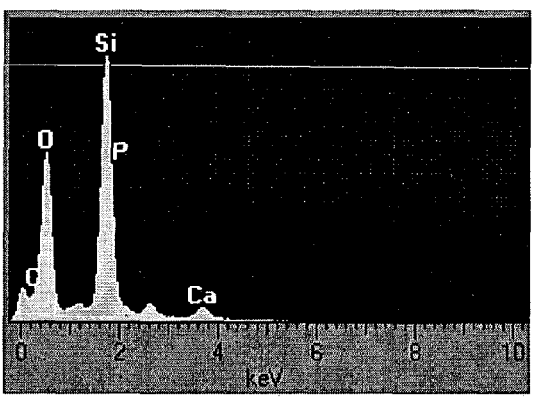
Figure 6F:
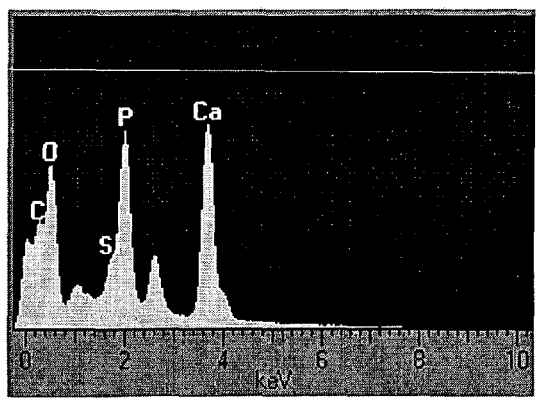

Gelled 77S BG fibers (FIG. 4) exhibited a 42.5% mass loss from 0-1100° C., with the thermal transitions being distributed into three regions (Brinker, C J and Scherer, G W. Sol-gel science: The physics and chemistry of sol-gel processing. San Diego: Academic Press; 1990). The initial transition region, denoted by the endothermic peak on the DTA curve, represents the evaporation of residual solvent and phys-adsorbed water. In this region between 25° C. and 150° C., the BG fibers experienced a 21.9% loss in mass. The large amount of solvent and water lost during this phase are attributable to the absence of drying and a relative humidity in excess of 70% during processing. The second transition confined to 150° C. to 500° C. accounted for a 14.6% loss in mass, primarily due to the loss of organic compounds associated with condensation of the residual metal alkoxides. The r-value was fixed at 1:2 in these sols, thus leaving two of the four ethoxy bonds unreacted. Both an endothermic and exothermic DTA peak within this temperature range are likely attributable to carbonization and oxidation, respectively. The final transition region from 500° C. to 1000° C. has a total mass loss of 3.1%. In this region 2 endothermic peaks on the DTA curve were observed at ~770° C. and 975° C., which may be ascribed to a small amount of residual $CaCl_2$ or the glass transition of the material.

Example 3

In Vitro Bioactivity

Determination of in vitro bioactivity of the fibers was performed in a simulated body fluid (SBF). The SBF was prepared by dissolving NaCl, $NaHCO_3$, KCl, $K_2HPO_4$, $MgCl_2*2H_2O$, $CaCl_2*2H_2O$, and $Na_2SO_4$ in ultrapure water (Kokubo, T et al., *Journal of Biomedical Materials Research*, 1990, 24:721-734). The concentrations of the ions in the SBF are listed in Table 1. Approximately 50 mg of fibers were submerged in 2.5 mL of SBF and incubated at 37° C. Fibers were maintained under quiescent conditions for 1, 5, 10, 20 and 30 days. The SBF was changed every other day for the first 10 days and then every fifth day thereafter. Fibers were examined under scanning electron micography (SEM) and the presence of hydroxyapatite was confirmed using EDX and X-ray analysis. A Phillips APD 3720 X-ray powder diffractometer was used to analyze samples with CuKα radiation (40 kV and 20 mA). XRD spectra were obtained over a 2θ range of 10-60° with a step size of 0.02° and scan rate of 0.02°/sec.

TABLE 1

Ionic concentrations of SBF

| Ion | Concentration (mM) |
| --- | --- |
| $Na^+$ | 1.42E+02 |
| $K^+$ | 5.00E+00 |
| $Mg^{+2}$ | 2.01E+00 |
| $Ca^{+2}$ | 2.50E+00 |
| $Cl^-$ | 1.49E+02 |
| $HCO_3^-$ | 4.17E+00 |

TABLE 1-continued

Ionic concentrations of SBF

| Ion | Concentration (mM) |
| --- | --- |
| $HPO_4^{-2}$ | 9.98E-01 |
| $SO_4^{-2}$ | 5.00E-01 |

SEM analysis of 77S Bioglass fibers in FIG. 5 reveals crystal formation 24 hours following submersion of fibers in SBF. Both the number and size of the crystals on the fiber surface increase following extended periods in SBF. Small crystals present after 1 day in SBF (FIG. 5B) preceded larger crystals seen on fibers submerged for 5 days (FIG. 5C). At 10 (FIG. 5D), 20 (FIG. 5E), and 30 (FIG. 5F) days the formation of larger crystal structures can be seen. The morphology of the crystals ranged from cuboidal (FIG. 5B and FIG. 5C) to needle like (FIG. 5D) to larger aggregations of many smaller crystallites (FIGS. 5E and 5F). EDX spot analysis of the crystals (FIGS. 5B-5F) and BG fibers (FIG. 5A) showed peaks at 1.5, 1.75, 1.8, and 3.75 keV representing the presence of oxygen, silicon, phosphorous, and calcium, respectively. A peak at 0.1 keV was also present from the carbon coating. The composition of the crystals was shown to exhibit elevated amounts of calcium, phosphorous and oxygen (the primary constituents of HA) when compared to unreacted Bioglass fibers.

FIGS. 6A-6F show EDX Spectra of fibers (FIG. 6A) and crystals (FIGS. 6B-6F) seen in the SEM images shown in FIG. 5. The presence of oxygen, silicon, phosphorous, and calcium are shown in both the fibers as well as the crystals.

Figure 7:
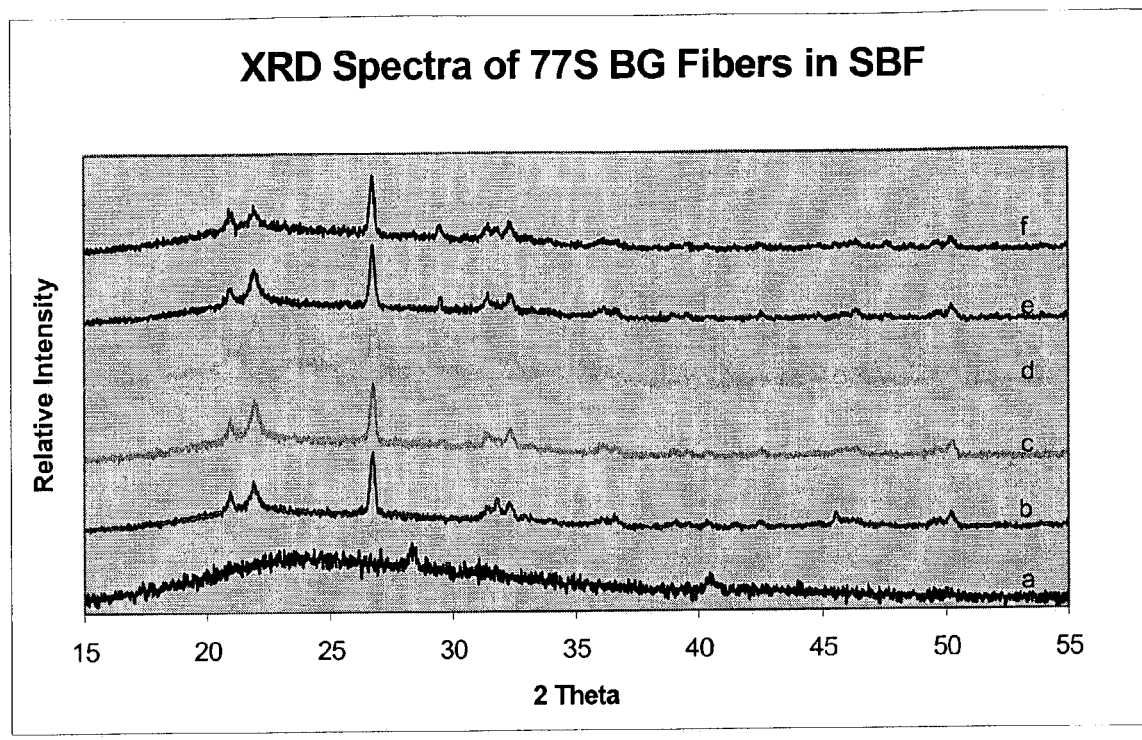
FIG. 7 shows XRD spectra of 77S Bioglass fibers in SBF for a) 0, b) 1, c) 5, d) 10, e) 20 and f) 30 days.

The presence of HA was further confirmed from XRD analysis. The spectra of the BG fibers can be seen in FIG. 7. Peaks at 2 theta values of 26°, 31-32°, and 50° characteristic of HA (Yuan, H et al., *Journal of Biomedical Materials Research, Applied Biomaterials*, 2001, 58:270-276; Smith et al. JCPDS International Center for Diffraction Data. Calcium phosphate hydroxide, CAS #1306-06-5.1996) were visible in all samples, with the most prominent peak coming at 26°. All fiber samples submerged in SBF also show a small peak at 37°, corresponding to the presence of CaO. Two additional peaks at ~21° were also seen in these samples.

Example 4

Cell Culture on Bioactive Glass Fibers

Fiber constructs of different porosities were prepared by packing varying masses of the bioactive glass fibers into constructs composed of a polypropylene ring and mica disk (PP/mica). The constructs had an average volume of 122.0±7.6 $mm^3$, and were loaded with 0, 10, 20, 40 or 60 mg of fibers. The density of the 77S BG fibers was determined from Archimedes method using a density apparatus obtained from Mettler Toledo. From the density, the volume of the fibers could be determined and compared with construct volume. Three masses were recorded; the mass of the fibers on the pan ($m_1$), the mass of the fibers hanging from the apparatus ($m_2$), and the mass of the fibers when submerged in ethanol. The difference of $m_2-m_3$ thus represented the mass of the displaced fluid, which in turn correlated to the sample volume. The density was then calculated from the following formula, accounting for the density of ethanol:

$$\delta = m_1/(m_2-m_3) \times 0.801$$

Male Wistar rats (~200 g in weight) were obtained. Both femurs were harvested and soaked in α medium supplemented with additional antibiotic. Post harvesting, the epiphyses of the femurs were removed to expose the marrow cavity, which was flushed with 25 mL of medium. The mixture of cells and medium was passaged through an 18G needle until sufficient dissagregation of the marrow plug was achieved. Alpha medium was prepared by adding ascorbic acid (50 μg/mL), glutamine, β Glycerophosphate, gentimycin, penicillin, and fetal bovine serum (15%) to Minimum Essential Eagle Medium.

Cells were passaged 2 times at 7 and 10 days and seeded onto the fiber constructs on the 13$^{th}$ day. Each construct was seeded with 1 mL of cells. Prior to seeding fibers and constructs were steam sterilized, wetted with ethanol, rinsed 3× with Hanks BSS, and soaked in fibronectin (5 μg/mL) for 1 hour. The cells were subsequently cultured for 3, 7, 10, 14 and 21 days after which point they were counted using a Beckman-Coulter Multisizer III. A 500 μL sample volume was analyzed at a flow rate of ~38 μL/sec.

The calculated density of the fibers was found to be 1.70±0.03 g/cc. The volumes of the various masses of fibers along with the corresponding porosities of the constructs are listed in Table 2. Porosity was defined as the fiber volume divided by the construct volume. The constructs exhibited porosity values ranging from 70-100%.

TABLE 2

Volume of fibers and relative porosity in the PP/Mica constructs used for MSC culture.

| Fiber Mass mg | Fiber Volume cc | Porosity % |
|---|---|---|
| 0 | 0.00E+00 | 100.0 |
| 10 | 5.88E−03 | 95.2 |
| 20 | 1.18E−02 | 90.4 |
| 40 | 2.35E−02 | 80.7 |
| 60 | 3.53E−02 | 71.1 |

Rat MSCs were successfully cultured on 77S BG fibers. The rate of proliferation and the total number of cells was found to depend on both the porosity of the scaffold and the time in culture. The concentration of cells was shown to increase as the spacing between the fibers decreased. The difference in cell concentration between the 10 mg and 20 mg samples was much less than the differences between the remaining adjacent groups as can be seen in FIG. 8. This may be related to similarities in the density of the two samples, as the 10 mg sample did not completely fill the construct. Addition of another 10 mg was added to the top of the 10 mg sample, and additional packing of the fibers to fill the construct was less severe than in the remaining samples.

The 60 mg sample showed the greatest number of cells and was also the first to reach a level of equilibrium. The concentration in the 60 mg sample leveled off after 14 days in culture, indicating the growth of cells to confluence, at which point differentiation was likely achieved. The remaining samples continued to proliferate after day 14, although the rate during this period was less significant than prior to day 14. At day 21 both the 20 and 40 mg samples were approaching the concentrations found on the 60 mg sample. An inconsistency seen in the 3 day sample without fibers is likely attributable to an excess in the number of cells seeded into the construct compared to the remaining samples.

FIG. 9 demonstrates the proliferation of the cells on the fiber constructs as a function of construct porosity. Samples exhibited an increase in proliferation with a decrease in porosity. In the majority of samples the increase in cell number was the most significant in the regions of 100-95% and 80-70% porosity. The increased number of cells for the higher density samples is likely attributable to a decrease in spacing between the fibers as well as an increase in total surface area. Additional packing of fibers into the constructs resulted in shorter spacing between adjacent fibers as well as an increase in available surface area. Closer packing of the fibers thus allowed the cells to bridge the gaps between the fibers, resulting in less compaction and prolonged differentiation. This dispersion of fibers that allowed for an expansion in available space for cell growth coupled with the preservation of the cells in an undifferentiated state led to increased proliferation for extended periods.

Example 5

Multi-Fiber Organized Scaffolds

The compositions of the subject invention can be formulated into randomly oriented scaffolds or organized scaffolds for tissue growth. In order to determine how organizing many fibers in a parallel array will allow the influence of their cooperative presence (e.g., whether they enhance ECM deposition compared to a single fiber), multi-fiber constructs were made from 7-0 MAXON sutures (DAVIS & GECK). The results obtained using the multi-fiber organized scaffolds composed of MAXON sutures can be extrapolated to scaffolds of the subject invention which are produced from a bioactive glass sol incorporating a viscosity-modifying polymer. Thus, the determinations made as to the relationship between fiber orientation and promotion of tissue growth can be extended to the sol-gel derived bioactive glass fibers and compositions of the subject invention.

Clear polyglactin (MAXON, Davis and Geck) fibers of 5-0 (~140 μm diameter), 6-0 (~99 μm diameter) and 7-0 (~79 μm diameter) were used for light microscopy studies.

Culture materials included α-minimal essential medium (Sigma, M0894) with 15% fetal bovine serum (Sigma, F4135), 50 mg/ml ascorbic acid (Sigma, A4034), 10 mM β-glycerophosphate (Sigma, G9891), antibiotics (0.1 mg/ml penicillin G, 0.05 mg/ml gentamicin and 0.3 mg/ml fungizone) and $10^{-8}$ M dexamethasone (Sigma, D2915). Bovine Fibronectin ~25 ug/ml (Sigma, F1141) was used to soak constructs prior to cell seeding, thus making fiber surfaces more amenable to cell adhesion. After soaking, Fn solution was pipetted off and cells were seeded directly onto constructs.

It should be understood that, although fibronectin was utilized to render the MAXON fiber surface amenable to cell adhesion, utilization of fibronectin on the sol-gel derived bioactive glass fibers of the subject invention is not required; however, fibronectin can be applied to the bioactive glass fibers of the subject invention if desired.

Prior to being incorporated into constructs, fibers were exposed to a 50 watt Argon plasma for 2 minutes at 50 milliTorr. MSCs were collected from both femora of grown, Sprague Dawley rats (~150-300 g). Constructs were seeded at ~1.5-2.0×$10^5$ cells/ml. Seeding at this density was done to increase the numbers of cells initially settling on the construct, which would allow a more rapid development of cell layers and overall a more timely series of experiments.

In order to insure that proper spacing was achieved between fibers, a new apparatus was designed and constructed. Pictures of the micromanipulating device of the present invention are shown in FIGS. 27A-27D. The device operates as a simple lever that translated the relatively large movements of the handle (a syringe barrel) through the pivot point to the actual manipulating portion of the device (a 1 inch 30 gauge needle). Because the handle of the device was much longer than that of the manipulator, the movements of the manipulator were much reduced with respect to the handle's movement. Fiber supporting means, tension means, and means for producing a pivot point are shown in FIGS. 27A-27D. A structure suitable for automating the micromanipulating device of the present invention should be readily apparent to those of ordinary skill in the art.

The micromanipulator was mounted onto an inverted microscope with a calibrated micrometer eyepiece (FIG. 27A). Through an opening in the stage of the micromanipulator it was possible to view fibers strung across the device. Polystyrene support rings, to which the fibers were glued, could be inserted underneath the fibers, while fibers were kept under constant tension by weights of ~29 grams on each side.

Using the micromanipulator, fibers were positioned to the correct spacing (either 25 microns, or 50 microns) and cemented to the polystyrene support ring using α-methylcyanoacrylate. Once secured to the support ring, excess fiber material was clipped from the multi-fiber construct. A parallel array multi-fiber construct prepared with this method is shown in FIGS. 11A and 11B. FIG. 11C shows a multi-layer multi-fiber construct with four parallel arrays of 7-0 fibers overlapping each other at a central point. Multi-fiber constructs were made with 45 degree angles between each successive layer.

After assembly constructs were left in a laminar flow hood overnight to allow cyanoacrylate to completely polymerize. Constructs were then mounted in 24 well plates using heated implement and immersed in 10% bleach for 30 minutes followed by two rinses in absolute ethanol. Rinsing with ethanol was followed by a 24 hour soak in ethanol under a 254 nm UV lamp.

Stainless steel specimens were cut into rectangles with the dimensions of 7 mm×12 mm then clamped in a pair of hemostats in the middle of their longest dimension and one side was pulled with a pair of pliers (FIG. 12A). Applying tension to one half of the construct led to the weave of the screens being elongated in the direction of the force creating parallelograms with the desired acute and obtuse angles (FIG. 12B). Angled screens were evaluated to determine the resulting acute angles leading to a mean value of 63.8 degrees with a standard deviation of 9.8 degrees (n=90 measurements). Identical measurements performed on the unstretched portions of the screens (FIG. 12C) led to a mean value of 89.3 degrees with a standard deviation of 2.1 (n=90 measurements). Screens were then autoclaved and placed in culture for 10 days.

Specimens were cultured for 21 days then fixed in 3% glutaraldehyde in phosphate buffered saline at pH 7.4 for 3 hours. 4% $OsO_4$ was used for post-fixation and samples were placed in this solution for 10 minutes followed directly in immersion in 30% EtOH the first stage in a serial ethanolic dehydration passing through 50%, 70%, 90% and finally 100% EtOH. After fixation and dehydration, samples were embedded in epon 828 hardened with Jeffamine D-230 in a stoichimetric ratio of 1.1:1.0, Jeffamine D-230: epon 828. Epon with specimens was allowed to cure at room temperature overnight followed by oven curing at 60 degree Celsius for 24 hours. Embedded samples were sectioned using a Leica ultracut microtome at ~250 nm, stained with uranyl acetate and lead citrate, then viewed with a JEOL 200 CX transmission electron microscope at 200 kV. Von Kossa Staining was performed.

The effect of weaving angle on mineralization was analyzed using the binomial parameter z-test. This is a test designed to measure the probabilities associated with experiments that are quantified in a yes, or no manner. Mineralization, or nodule formation within bridges formed at the locations of the angles made by interwoven fibers was the measured dependent variable. To perform these measurements, each parallelogram in the case of the stretched portions of the screens was divided into quadrants (FIG. 13). Similarly the square holes of the unstretched portions of the screens were divided into quadrants (FIG. 13). If mineralized nodules were seen in the quadrants associated with acute angles, it was considered a "Yes", or positive result, while nodules in the obtuse regions were considered "No". Measurements in the unstretched regions were performed in the same orientation as the long axis of the parallelograms as indicated by the arrow in FIG. 13. In the 90 degree region the same criteria were used to determine "Yes", or "No" data, that is the presence of mineralization was measured in quadrants that corresponded to the quadrants in the stretched portions of the screens (this is indicated by the hatching seen in the quadrants in FIG. 13).

In the 90 degree control screens, though bridging is somewhat regular in the alternating eye shape motif, it should occur just as often in one direction as the other direction. Under this experimental condition the probability ($\pi_0$) of bridging and therefore mineralization occurring is just as likely in the "Yes" quadrants as the "No". Since the holes are divided into four quadrants, two that equal yes and two that equal no, the probability ($\pi_0$) that bridging and mineralization will occur in each is the same and is $\pi_0=0.5$ the control probability.

If bridging and hence mineralization is not affected by the angles of the fibers then the likelihood that it would occur on acute angles is equal to the probability seen on obtuse angles. This would be the same as that seen in the controls. The hypothesis, however, is that bridging and hence mineralization will occur preferentially in the quadrants associated with the acute angles, or more often than that seen on the control portions of the screen ($\pi_{acute} > \pi_0$). The complete statistical test is reproduced below.

Null Hypothesis: $\pi = \pi_0$  Where: $\pi_0 = 0.5$
Alternate Hypothesis: $\pi_{angle} > \pi_0$ Test Statistic: $z = \dfrac{\pi_{angle} - \pi_0}{\sigma_{\pi_{angle}}}$  Where: $\sigma_{\pi_{angle}} = \sqrt{\dfrac{\pi_0 \cdot (1-\pi_0)}{n}}$ Reject Null Hypothesis if: $z > z_\alpha$  Where: $z_\alpha$ is the probability $\alpha$ of type 1 error.

Results

MAXON Bridging Day 3

Single fiber constructs exhibited many cells adhering to their surfaces indicating they were well seeded.

25 micron parallel arrays all showed at lease one case of bridging between fibers sometimes 3 or 4 examples of it were present.

55 micron parallel arrays had a level of cellular attachment that was similar to the single fiber constructs. It appeared that each fiber was acting independently of the others. There was one example of bridging near the periphery of the constructs where the fibers were bound to the support ring.

MAXON Bridging Day 6

Single fiber constructs were completely covered with cells and some had developed thick areas of multi-layering.

25 micron parallel arrays showed some examples of inter-fiber bridging across the whole length of the construct from one end of the fibers to the other. There were spontaneous inter-fiber bridges forming mid-fiber on every one of the constructs. These inter-fiber bridges were abundantly evident and not the result of any physical pathway between fibers.

55 micron parallel arrays had become fully covered with cells and exhibited some bridging, but only at the ends of the fibers near where the constructs were bound to the support ring. This bridging appeared to be due to the physical pathway provided by the support ring and was not very extensive.

MAXON Bridging Day 8

Single fiber constructs had developed very thick cells layers that were approximately 20-25 microns thick as measured by micrometer eyepiece, which led to a thickness of fiber plus cell layer totaling ~120-125 microns. One construct demonstrated a contraction of cells along its length that led to a thick cellular layer ~35 microns thick around the entire circumference of the fiber (FIG. 14B). This contraction proceeded from both ends of the construct toward the center.

25 micron parallel arrays were all an estimated 75-90% of total volume available between fibers was bridged.

55 micron parallel arrays had developed thick multi-layering on individual fibers with bridging at the ends of the constructs. Only about 20% of total available volume was bridged between fibers and only at the ends of the fibers.

MAXON Bridging Day 10

Single fiber constructs demonstrated no significant change, except the previously noted contraction along one fiber had progressed.

25 micron parallel arrays 3 of 4 constructs were completely bridged. One area of one construct had undergone a contractile process similar to that seen on the single fiber construct (data not shown).

55 micron parallel arrays exhibited little change except the development of contractile processes on some fibers.

MAXON Bridging Day 11

Single fiber constructs showed no remarkable change except contraction on the aforementioned fiber had progressed to such a degree that all the cells were balled at the center of the fiber (image of FIG. 14B taken at this time point). One remarkable feature was the bridging that had developed where the fiber was attached to the support ring. This response to the topography of the ring and fiber combination led to a bridge that transitioned from the topography of the ring to that of the fiber in a continuous and gradual manner.

25 micron parallel arrays showed no remarkable change from day 10.

55 micron parallel arrays 1 construct had developed a thick multi-cellular bridge where a contractile balling of cells had gotten near to the adjacent fiber. There was no physical pathway for the cells to follow and this occurred mid-fiber, but only on one construct.

Cell angle and spacing distance seemed to be related. In FIGS. 15A and 15B, the cells were oriented in the directions of the fibers, but also seemed angled to a degree necessary to span the distance between fibers. Because the fibers were farther apart on the 55 micron constructs, the cells seemed to be at a more obtuse angle than that seen for bridging between 25 micron constructs.

Multi-Layer Constructs

Bridging between fibers progressed in a manner analogous to that seen on parallel arrays. Bridging between layers was very robust and showed a marked propensity for forming at the sites where fibers formed acute angles (FIGS. 18A and 18B). FIG. 18B shows examples of bridging between layers, where it was possible for bridging to occur in either direction on the fiber. Bridging occurred more prominently on the acute side of the intersection of the fibers in these situations.

Stainless Steel Bridging Day 3

Many cells were evident on the stainless steel fibers composing the weave of the mesh and unicellular bridges had begun to form.

Stainless Steel Bridging Day 6

Cell growth was robust and obvious with many examples of unicellular bridging. Bridging occurred at the junctions of the fibers and in the case of the angled portions of the screens, the bridging was subjectively much greater on the acute angles versus the obtuse. Bridging also began to occur sooner than that seen on the 90 degree portions of screen.

Stainless Steel Bridging Day 8

Cell growth and bridging continued in a very rapid manner and there were instances of holes being completely filled with bridged cells. Occasional mineralized nodules were seen in the bodies of the bridges.

Stainless Steel Bridging Day 10 (Mineralization Analysis)

Screens were removed from culture fixed then in 3% glutaraldehyde. After von Kossa staining, screens were analyzed for mineralization. A representative image of bridging and mineralization on the angled portions of the screens is shown.

The probability of mineralization was shown to be significantly greater on the acute angles than mineralization seen on the obtuse angles ($P<0.0001$). The probability of mineralization seen on the 90 degree portions of the screen, however, was not significantly different for either orientation.

Overall, the probability of mineralization was shown to be greater on the quadrants of screen that included acute angles versus obtuse, while on the 90 angle portions it was equally likely to occur in any quadrant (data summarized in Table 3). Mineralization preferentially occurred on the acute angles of stainless steel screens after being cultured in a RMSC system for 10 days.

TABLE 3

Probability of Mineralization

|  | Yes | No | Probability ($\pi$) | $\sigma_\pi$ | "z" value | $z_\alpha$ (for $\alpha = 0.99$) | Significant |
| --- | --- | --- | --- | --- | --- | --- | --- |
| Angled | 65 | 21 | 0.76 | 0.054 | 4.74 | 2.57 | Yes |
| Squares | 35 | 31 | 0.53 | 0.062 | 0.48 | 2.57 | No |

Transmission Electron Microscopy of 7-0 Single Fiber

FIG. 20 shows a cross sectional view of a single 7-0 fiber cultured for 21 days in the RMSC system. This montage of micrographs reveals multi-layering composed of a depth of about 3-5 cells. Cellular interconnections are evident.

Length wise sections of the same single fiber construct are shown in FIG. 21. Again cellular interconnections are evident and what appears to be collagen is being deposited between cell layers in the extra-cellular space. Cells are much elongated, indicating contact guidance effect of the 7-0 fiber diameter.

Transmission Electron Microscopy of 7-0 25 Micron Spaced Parallel Array

The sample shown in FIG. 16C was cross-sectioned near the ends of the fibers where they were secured to the support ring and had not been contracted, or pulled together as occurred nearer the center of the construct. FIG. 22 shows an electron micrograph montage of a representative bridge that occurred between fibers. The curve of the fibers is evident on either side of the bridge, which formed on the top of the fiber array, or on the upper part of the array as it sat in the culture well. There were very few cells in the space below the bridge as it is shown indicating that a strong majority of cells were present were involved in the inter-fiber bridging in the area pictured. The thickness of the bridge appeared greater than that seen on single fibers and did not seem as tightly associated in their multilayering. There appeared to be more space between cells than that seen on the surfaces of the single fibers. In addition, cells appeared to be more flattened and thinner in nature than that seen on the single fiber.

Transmission Electron Microscopy of Contracted 7-0 25 Micron Parallel Array

The sample shown in FIG. 8C was cross-sectioned near the center of the construct in an area where the cells had contracted, or pulled together the fibers. The fibers of the construct were pulled virtually all the way together and the intervening space between them was completely filled with cells and ECM (FIG. 23). There appeared to be two main influences on cell orientation and multi-layering, the influence of bridging which was seen on the cells composing the upper most portions of the cellular aggregate and the fibers. Fiber induced cellular orientation followed a similar pattern to that seen on single fiber samples with a cellular multilayer that was 3-5 cells thick. Where the bridge and the cells associated with the fiber meet, there are multilayers that may be as deep as 10-12 cells. In the center of the bridge cell layers extend to entire distance to the location where the fibers are brought together (FIG. 23).

Cells are highly flattened and again appear to have more space between them than the cells seen on single fiber constructs. A direct comparison can be made by looking at cells on the fiber surface of the fibers versus those suspended between the fibers composing the body of the bridge. What appears to be fibrillar ECM deposits are seen between the cell layers and is abundant in the large areas of space between cells in the bridge (FIG. 23 inset). Cellular interconnection is again prominent, perhaps even more than any other experimental condition examined so far.

Longitudinal sections of the same sample taken from the area immediately adjacent to that shown in FIG. 23 reveal the most organized ECM and cellular orientation seen of all samples studied. Collagen fibrils are abundant in the extracellular space between the cells (FIG. 24 arrows). Insets show collagen fibrils at high magnification. Cell orientation is also highly apparent indicating that cells involved in the bridging process are flattened and extended in the direction of the fiber constructs in a very ordered and oriented manner (arrowheads). Fibrils were confirmed to be collagen be the presence of the characteristic banding pattern that existed on the scale of 60-80 nanometers (FIG. 25).

As mentioned earlier in this work, woven fibers when used as tissue scaffolds offer a number of advantages. Using appropriate processing methods, individual fibers can be made with remarkably robust tensile strength [von Falkai 1995, Postema 1990a Postema 1990b], more importantly, however, these fibers can be organized in a woven construct that is very rigid [Wintermantel 1996]. It was hypothesized that controlled arrays of fibers would be capable of organizing cells and their ECM products directionally over large surface areas, or volumes. The results described herein provide strong evidence that this hypothesis is indeed correct.

A strong contact guidance in response to the diameter of fibers cells were grown on was seen on the fibers composing the parallel arrays in this study. Elongation of cells on the fibers was apparent on all constructs regardless of the spacing between their fibers. This phenomenon, however, was especially apparent on the constructs with 55 micron spacing as bridging on these constructs was sparse and each fiber acted virtually independently from the others. In many ways the constructs with 55 micron spacing acted as a collection of single fibers.

Though there is little material in the literature addressing the topic of bridging the ability of cells of mesenchymal origin to migrate across spacing has received some study. Murray et al. 1991, studied the migration of anterior cruciate ligament cells onto synthetic scaffold materials and showed that migration was inhibited by the presence of gaps between the ligamentous tissue used as a cell source and the scaffold. These gaps were effective at preventing migration when they were separated by as little as a 50 micron spacing distance. This matches well with the current results, which showed bridging on 55 micron constructs, but only as long as a physical path was present like the one found at the ends of the constructs where the fibers were secured. There were no cases of spontaneous bridging across the 55 um gaps between fibers like that seen on the parallel arrays with 25 micron spacing.

The cells elongated and oriented on individual fibers of parallel arrays with 25 micron spacing, as well. However, spontaneous bridging between fibers became a significant and added factor as early as the third and sixth days. Effectively, cells were being guided not only by individual fibers they were growing on as seen initially, but also by the way they were able to bridge and fill the distance between fibers (FIG. 15A). 25 micron spacing allowed the development of what was essentially a layer, or lamella of cells and ECM, which extended for multi-millimeter length scales (5-6 mm, the length of the multi-fiber constructs as seen in FIGS. 11A-11C) and covering fiber surfaces and filling inter-fiber spaces.

As expected, single fibers themselves directed cell growth and organization of the cells and ECM (FIGS. 20 and 21). More importantly, the electron micrographs show that cells composing the bridges were also oriented and directed in the spaces between fibers (FIGS. 22 and 23). This cellular orientation appeared to be even greater than that seen on single fibers as the cells were more noticeably flattened in their cross sectional view. This shows bridging, which is a hierarchical cellular activity in that it occurs in addition to the normal multi-layering seen on fibers, is directed by the macrotopographies provided by the combination of two or more single fibers.

This statement is further supported by the data obtained by RMSC growth on angled stainless steel screens. It is seen from the robust statistical results that formation of mineralized nodules within bridges occurs preferentially on the inter-fiber angles that are acute in nature. 90 degree angle inter-fiber junctions on the other hand led to a random formation of mineralized nodules. Bridging preferentially occurred on the acute angles, or distances that were shorter that their 90 degree counterparts in such a way that it led to mineralization that was far greater. In addition to showing another aspect of controlled bridging as a controllable phenomenon, these results show the ability to direct and control mineralization within the spaces of a scaffold or matrix.

Controlled collagen deposition is also achieved in this system using the macrotopography of multi-fiber parallel arrays. The MSC type used in this study deposits collagen in the extra-cellular spaces existing between cell layers (Aronow 1990, Gerstenfeld 1988, Luegmayr 1996 & Nefussi 1985). It has been shown repeatedly that this deposition occurs in alternating orthogonal orientations between adjacent cell layers, or layers that are built up on top of each other when grown on flat 2-D surfaces (Aronow 1990, Gerstenfeld 1988 & Nefussi 1985). This is not the case in this bridging system. Orientation of fibrils at 21 days of culture in a RMSC system showed collagen that was in parallel orientations with the fibers between every extra-cellular layer (FIGS. 23 and 24).

Overall with the evidence of these studies it is quite apparent that the direction of cellular orientation, collagen deposition and mineralization are capable of being controlled by designed fiber scaffolds. The spacing of fibers influences the ability of cells to bridge between them. Bridging between fibers of appropriate spacing is seen to be a highly directed activity leading to the deposition of collagen in a manner that appears more oriented than that seen on flat surface, or surfaces with microtopographies. Furthermore the angle between fibers, a critical aspect of fiber weaving, has been shown to influence the bridging and hence the spatial location of mineralization. All these aspects of control are possible through an understanding of the multi-layering seen in this system and more importantly the bridging phenomenon this cell type undergoes. Not only do these studies show the feasibility of fiber-based scaffolds in bone replacement tissue engineering, they provide deep insight into the bridging process itself, which appears to be primarily responsible for these effects.

Thus, in another aspect, the invention includes fiber constructs having fiber spacing and/or interfiber angles identified herein as capable of promoting cell growth. For example, the fiber constructs can be polymeric in nature, such as polyglactin (MAXON), or bioactive glass fibers. The fiber constructs can comprise a sufficient number of acute angle (<90°) interfiber junctions so as to provide increased control of cell growth and cell product (e.g., ECM) deposition within the spaces of the scaffold or matrix, as demonstrated in Table 3.

RMSCs viewed were interconnected in every instance of specimen studied via TEM, which indicates these cells form interconnected networks. This is supported by many studies in the literature including the studies of the cellular interconnections known as gap junctions, which are actual physical connections between cells. In addition, the autocrine and paracrine interactions that govern many aspects of bone cell communication indicate they are interconnected networks. It is not apparent from this data if the cellular interconnections are sites for cellular communication, though they are almost certainly sites of mechanical attachment that allow the networks to form.

Studies performed on flat surfaces match up well with the multilayering behavior observed. Layers formed on the surfaces of single fibers with thickness of about 3-5 cells with little space between layers. These aspects of multilayering and extracellular space have also been seen by in a virtually identical manner many times in the literature (Aronow 1990, Gerstenfeld 1988, Luegmayr 1996 & Nefussi 1985). Organization of collagen by the single fiber surface, however, is not consistent with these studies in that it orients collagen on each layer parallel to the fiber it is grown on. Flat surfaces showed the alternating pattern mentioned previously.

Bridging data diverges even more significantly from these trends. Though the formation of physical inter-cellular connections remains leading to a cellular matrix, the space between cell layers is much greater. This result makes sense if one considers the differences in topographies available between the flat surface and that which exhibits a macrotopography. On a flat surface, all cells must bind to that surface, either directly, or indirectly (i.e., indirectly by upper layers binding to the lower layers which in turn bind that surface, as shown in FIG. 25B). Given the fact that these cells require a tension generation for their proper development and differentiation, the only way it can be achieved is by creating force in the directions they are flattened. It seems quite likely that this well documented contractile force generation on a 2-D surface leads to a compressive component, decreasing space between cells.

In the bridged MSCs on the other hand, cellular elongation and flattening is greater (FIGS. 23 and 24). This indicates that cells involved in bridging may be capable of achieving greater tension and this more flattening with the advantage of a second site of topography. Also, the presence of more than one surface for attachment provides a way of developing tension without compressing extracellular spaces (FIG. 25). This space is the site of collagen deposition as seen from the TEM data, therefore this increased space may be available for the deposition of collagen. 3-D scaffolds used in tissue engineering studies have shown increased amounts of collagen and ECM production when compared to flat surfaces (Akhonayri 1999). This increased amount of space may be the reason, or at least part of the reason for this increased production ability.

Scaffolds where tension development is not possible (i.e. scaffolds contract but are not anchored so tension development is not possible) also show markedly less ECM production when compared to anchored scaffolds (Nakagawa 1989). This fact fits with the current theory of the role extracellular space plays in that the contraction seen in unanchored scaffolds would eliminate excess extra-cellular space, as well.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof may be made by persons skilled in the art without departing from the scope of the present claims.

We claim:

1. A bioactive glass composite, comprising;
a biocompatible polymer,
a bioactive glass including at least one calcium, and at least one phosphorous molecular species; the biocompatible polymer being reacted with the bioactive glass, wherein said calcium and said phosphorous molecular species are not crystalline.

2. The composite of claim 1, wherein said composite is in the form of microfibers, said fibers having a diameter less than 100 μm.

3. The composite of claim 1, wherein said composite is in the form of particles, microspheres, or coatings.

4. The composite of claim 2, wherein cells when seeded proliferate on said fibers.

5. The composite of claim 4, wherein said cells are stem cells.

6. The composite of claim 5, wherein said stem cells proliferate in the absence of any growth hormones.

7. The composite of claim 2, wherein said fibers are substantially equally spaced to form an organized scaffold.

8. The composite of claim 7, wherein said equal spacing is less than 50 μm.

9. The composite of claim 7, wherein said equal spacing is less than 25 μm.

10. The composite of claim 1, wherein a porosity of said composition is at least 50%.

11. The composite of claim 1, further comprising at least one biologically active agent.

12. The composite of claim 11, wherein said composition forms an encapsulation layer around said biological agent.

13. The composite of claim 11, wherein said biologically active agent is adsorbed onto the surface of said composition or chemically attached to a surface of said composition.

14. The composite of claim 12, wherein said encapsulated biologically active agent is in the form of at least one selected from the group consisting of microcapsules, microspheres, microparticles, microfibers, sol gel matrices, and reinforcing fibers.

15. The composite of claim 12, wherein said encapsulation layer is continuous, wherein a sustained release profile of said biologically active agent is provided.

16. The composite of claim 1, further comprising at least one protein.

17. The composite of claim 16, wherein said protein comprises at least one selected from the group consisting of collagen (including cross-linked collagen), fibronectin, laminin, elastin (including cross-linked elastin), osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor.

18. The composite of claim 1, wherein said composition is disposed on a surface of or integrated within a medical device adapted for implantation into a patient.

19. The composite of claim 18, wherein said medical device is a prosthetic device.

20. A method of repairing hard or soft tissue defects, comprising the steps of:
applying a fiber composition comprising a biocompatible polymer, a bioactive glass including at least one calcium and at least one phosphorous molecular species to a defect site on a patient, wherein said calcium and said phosphorous molecular species are not crystalline.

21. The method of claim 20, wherein said composition is in the form of microfibers, said fibers having a diameter less than 100 μm.

22. The method of claim 20, wherein said fibers are substantially equally spaced to form an organized scaffold.

23. The method of claim 20, wherein said equal spacing is less than 50 μm.

24. The method of claim 20, where said composition is in the form of particles.

25. The method of claim 20, wherein cells proliferate on or around said composition in the absence of any growth hormones.

26. A method of forming a bioactive glass, comprising the steps of:
mixing a biocompatible polymer, a gelable inorganic base material, and at least one calcium and phosphorous molecular species, and
hydrolizing said mixture, wherein said calcium and said phosphorous molecular species are not crystalline.

27. The method of claim 26, further comprising the step of forming a plurality of fibers, wherein said forming process is at a temperature of no more than 200 C.

28. The method of claim 27, wherein said forming step comprises air-spraying or extruding.

29. The composite of claim 1, wherein said glass is a continuous phase inorganic network.

30. The composite of claim 1, wherein said bioactive glass comprises a gelled inorganic material containing at least one calcium and at least one phosphorous molecular species.

31. The composite of claim 30, wherein said gelled inorganic material comprises at least one gelled alkoxysilane.

32. The composite of claim 30, wherein said gelled inorganic material comprises at least one gelled non-alkoxysilane alkoxide selected from the group consisting of alurninates, titanates, and borates.

33. The composite of claim 1, wherein said biocompatible polymer comprises at least one selected from the group consisting of polyvinylpyrrolidone (PVP), polyethyleneimine (PEI), polycarboxylmethylcellulose (PCMC), polyethylenglycol (PEG), polypropylene oxide (PPO), polyvinylalcohol (PVA), polyacrylic acid (PAA), polymethylacrylic acid (PMAA), polystyrene sulfonic acid (PSSA), and gelatin.

* * * * *